(12) United States Patent
Younes

(10) Patent No.: US 8,910,633 B2
(45) Date of Patent: Dec. 16, 2014

(54) METHOD FOR ESTIMATING LEAKS FROM VENTILATOR CIRCUITS

(75) Inventor: Magdy Younes, Winnipeg (CA)

(73) Assignee: YRT Limited, Winnipeg, Manitoba (CA)

( * ) Notice: Subject to any disclaimer, the term of this patent is extended or adjusted under 35 U.S.C. 154(b) by 656 days.

(21) Appl. No.: 13/138,279

(22) PCT Filed: Jan. 29, 2010

(86) PCT No.: PCT/CA2010/000134
§ 371 (c)(1),
(2), (4) Date: Dec. 15, 2011

(87) PCT Pub. No.: WO2010/085895
PCT Pub. Date: Aug. 5, 2010

(65) Prior Publication Data
US 2012/0078542 A1    Mar. 29, 2012

Related U.S. Application Data

(60) Provisional application No. 61/202,123, filed on Jan. 29, 2009.

(51) Int. Cl.
*A61M 16/00* (2006.01)

(52) U.S. Cl.
CPC ....... *A61M 16/0051* (2013.01); *A61M 2205/52* (2013.01); *A61M 2205/50* (2013.01); *A61M 2016/0033* (2013.01); *A61M 2016/0027* (2013.01); *A61M 2016/0021* (2013.01); *A61M 2205/15* (2013.01)
USPC ............ 128/204.23; 128/200.24; 128/204.18; 128/204.21

(58) Field of Classification Search
CPC ....... G01F 1/684; G01F 1/6847; G01F 1/696; G01H 3/005; G01M 3/26; G01M 3/00; A61M 2205/15; A61M 16/0051
USPC ............ 128/200.24, 202.22, 204.18, 204.21, 128/204.23
See application file for complete search history.

(56) References Cited

U.S. PATENT DOCUMENTS

| 5,803,065 A | 9/1998 | Zrojkowski et al. | |
| 6,546,930 B1 * | 4/2003 | Emerson et al. | 128/204.21 |
| 7,798,143 B1 * | 9/2010 | Kirby | 128/204.18 |
| 7,918,223 B2 * | 4/2011 | Soliman et al. | 128/204.21 |

FOREIGN PATENT DOCUMENTS

| WO | WO 2008/025079 | 3/2008 |
| WO | WO 2009/123980 | 10/2009 |
| WO | WO 2010/085895 | 8/2010 |

* cited by examiner

*Primary Examiner* — Annette Dixon
(74) *Attorney, Agent, or Firm* — Sim & McBurney

(57) ABSTRACT

Gas leakage from a ventilator circuit and patient interface is estimated by a method that relies on breath-by-breath or time-to-time variability in the pattern of pressure delivery by the ventilator, comprising generating signals that correspond to pressure ($P_{CIRCUIT}$) and flow rate (Flow) in the ventilator circuit, integrating flow (Integrated Flow), measuring the change in Integrated Flow ($\Delta V$) over an INTERVAL extending from a selected point in the expiratory phase of a ventilator cycle to a selected point during the expiratory phase of a nearby ventilator cycle, repeating the measurement of $\Delta V$ for at least two said INTERVALs, processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALs and the corresponding differences in said index or indices of $P_{CIRCUIT}$, and establishing from said relation the leak rate at specified $P_{CIRCUIT}$ values.

32 Claims, 11 Drawing Sheets

METHOD FOR ESTIMATING LEAKS FROM VENTILATOR CIRCUITS

REFERENCE TO RELATED APPLICATIONS

This application is a U.S. National Phase filing under 35 USC 371 of PCT/CA2010/000134 filed Jan. 29, 2010 claiming priority under 35 USC 119(e) from U.S. Provisional Patent Application No. 61/202,123 filed Jan. 29, 2009.

FIELD OF INVENTION

The invention relates to ventilators.

BACKGROUND TO THE INVENTION

Ventilators are typically connected to patients via tubing and an interface. In invasive ventilation, the interface is usually a tube inserted in the patient's trachea (endotracheal tube; ET tube). A seal is usually maintained by inflating a cuff around the stem of the ET tube. In non-invasive ventilation (NIV), the interface is usually a mask or a helmet applied to the face/head around the patient's external airway (nose and/or mouth). A seal is maintained usually by applying appropriate tension to the straps holding the interface in place. In both invasive and non-invasive ventilation, the seal is at times imperfect resulting in air leaking from the ventilator circuit. In addition to these leaks at the interface, leaks can potentially arise from loose connections between different components of the tubing or defective tubing and, in the case of NIV, from deliberate leaks inserted in the tubing to act as a conduit for carbon dioxide removal. These different sources of leak display different relations between instantaneous pressure and leak flow. For example, with an orifice as the source of leak, leak flow increases as a function of the square root of pressure. With mask leaks, leak flow may increase linearly with flow or may increase disproportionately as pressure increases because the mask lifts away from the face, increasing the anatomical size of the leak. Thus, in practice, the relation between instantaneous pressure and leak flow is highly unpredictable.

Knowledge of the nature and magnitude of such leaks is important for the proper functioning of the ventilator. When the applied pressure is constant (for example, continuous positive airway pressure; CPAP) the leak is necessarily constant and can be readily estimated from the moving average of the flow signal. Since the amount of air entering the lungs during inspiration is roughly equal to the amount of air leaving the lungs during expiration, a moving average of flow rate over several breaths should be approximately zero in the absence of leaks. A positive average value indicates the presence of a leak and, because the leak is constant (since circuit pressure is constant), the magnitude of the moving average of flow rate reflects the magnitude of the constant leak.

The situation is quite different in ventilation modes in which the pressure applied to the patient is not constant (for example, bilevel support, proportional assist ventilation, volume cycled ventilation . . . etc). Here, the magnitude of the leak varies from time to time within each ventilator cycle depending on the instantaneous pressure in the circuit. Under these conditions, the moving average of flow rate continues to reflect the average leak but the value of the average leak no longer reflects the instantaneous leak at the different points in the cycle. Thus, average leak will overestimate the magnitude of leak during periods in which circuit pressure is below average, and vice versa. This could result in malfunction of the ventilator, particularly with respect to the times the ventilator is required to increase or decrease circuit pressure (triggering and cycling-off). For proper ventilator functioning it is necessary to know the relation between instantaneous circuit pressure and instantaneous leak. The present invention deals with an approach that determines said relation over the operating pressure range of the ventilation cycle.

Determination of the instantaneous relation between circuit pressure and leak has been problematic for the following reason. Flow rate is typically measured within the ventilator enclosure, usually at the points where the ventilating gas exits, and/or returns to the ventilator. The flow rate measured by the ventilator at any instant ($Flow_{(i)TOTAL}$) is the sum of flow rate into or out of the patient ($Flow_{(i)patient}$) and the flow rate going through the leak ($Flow_{(i)leak}$). Thus:

$$Flow_{(i)TOTAL} = Flow_{(i)patient} + Flow_{(i)leak}$$

As circuit pressure changes during the ventilator cycle $Flow_{(i)TOTAL}$ changes in part because $Flow_{(i)patient}$ changes and in part because $Flow_{(i)leak}$ also changes. In the course of a ventilator cycle $Flow_{(i)patient}$ changes in an unpredictable way, being subject not only to circuit pressure but also to the unknown time course of the patient's respiratory muscle pressure output ($P_{MUS}$) and patient's respiratory mechanics. Because both components of $Flow_{(i)TOTAL}$ change unpredictably with instantaneous pressure, it is necessary to independently determine the relation between instantaneous pressure and leak flow rate in order to be able to estimate $Flow_{(i)patient}$. It is knowledge of the patient's flow rate signal ($Flow_{(i)patient}$) that is critical in the operation of the ventilator as it is used to trigger and cycle-off the ventilator as well as for monitoring adequacy of the assist and patient performance.

To the writer's knowledge, currently the most advanced method for estimating instantaneous leak during a variable pressure cycle is the one patented and used by Respironics (U.S. Pat. No. 5,803,065). Here, the total leak across a whole breath, or a plurality of breaths, is measured from the difference between the integral of $Flow_{(i)TOTAL}$ at the beginning of a breath and at the beginning of a subsequent breath, one or more breaths removed. This difference is assumed to reflect the volume of air that leaked out during the interval ($\Delta V$). A certain mathematical function is then assumed for the relation between instantaneous pressure and instantaneous leak. The time course of pressure, processed according to this assumed function, is then integrated over the duration of the Interval. For example, if, as proposed in this prior art, the assumed function is [leak=$K \cdot P^{0.5}$], (i.e. leak is proportional to the square root of pressure), the integral of pressure, raised to the power 0.5 is calculated. The ratio $\Delta V$/integral of $P^{0.5}$ gives the value of K. Leak at any pressure can then be estimated from the leak equation according to the assumed function.

The above approach suffers from several drawbacks:

1) It is assumed that the volume difference between the beginning of a breath and the beginning of a subsequent breath (i.e. $\Delta V$) is exclusively related to leaks. This is not true as the patient's inhaled and exhaled volumes can differ substantially on a breath-by-breath basis. Thus, $\Delta V$ across one breath incorporates an unknown component related to true differences in patient's lung volume between the beginning of one breath and the beginning of a subsequent breath ($\Delta V_{PATIENT}$). This problem is addressed in the Respironics technology by integrating the flow rate and the processed pressure over several breaths, on the valid assumption that differences between inhaled and exhaled volumes cancel out over a reasonable number of ventilator cycles (lung volume cannot indefinitely continue to rise or fall.

2) The above treatment assumes that the leak occurs over the entire pressure range, beginning with any pressure above zero (atmospheric). While this is true with built-in leaks, such as those inserted in the tubing during NIV, it is not true for unintentional leaks at the interface. Here, the seal may be air tight up to a certain pressure (i.e. no leak up to a threshold pressure ($P_{THRESH}$)). The leak would then be a function of pressure above this threshold [leak=$K \cdot f(P-P_{THRESH})$]

3) Leaks often are derived from multiple sources. The treatment in this prior art assumes that one mathematical function can describe the overall leak even though such leak may be derived from multiple sources, each with its own function.

4) Most importantly, one needs to assume, a priori, the specific function that governs the relation between instantaneous pressure and instantaneous leak. In the prior art (U.S. Pat. No. 5,803,065) it was assumed that the function is a power function with the exponent being 0.5. Although this may accurately reflect the leak flow through a fixed orifice, naturally occurring leaks do not behave like fixed orifices. Rather, with the most common unintentional leaks, those at the interface (for example, insufficient tension in the mask straps), once pressure exceeds $P_{THRESH}$ leak dimensions increase as pressure increases. Thus, not only is the driving pressure increasing, but the resistance to flow through the leak is also decreasing. In my observations, such leaks can follow a number of functions and, even assuming a power function, the exponent can be far from 0.5. Since it is not possible to know a priori what function these unintentional leaks will follow, it is not possible to implement the prior art for all possible types of leak and expect acceptable accuracy.

In summary, the correct relation between $\Delta V$ and a pressure-dependent leak is:

$$\Delta V - \Delta V_{PATIENT} = K \cdot \int f(P-P_{THRESH})$$

Where, $\Delta V_{PATIENT}$ is the change in patient's lung volume between the two measurement points, K is the constant of proportionality, $P_{THRESH}$ is the pressure at which the leak begins, and $f$ is the specific function selected which may be any of several mathematical functions (for example, power, logarithmic, exponential, polynomial). In implementing the prior art it is not only necessary to know (or assume) the function type, but it is also necessary to specify the exponent of this function. Since neither the function, nor its exponent, nor $P_{THRESH}$ can be known a priori, it can thus be seen that the approach described in the prior art [i.e. $\Delta V = K \cdot \int P^{0.5}$] represents a great simplification and may be expected to provide erroneous instantaneous leak values in situations where the leak does not follow the behavior of fixed orifices.

SUMMARY OF THE INVENTION

In the present invention, no a priori assumptions are made about the function governing the relation between pressure and leak. Rather, this approach focuses on determining what function best describes the operative relation between circuit pressure and leak rate, regardless of its type. A number of algorithms are described herein to determine said relation. All these algorithms share in common the utilization of breath-by-breath, or time-to-time variability in the pattern of pressure delivery by the ventilator. Thus, the basic premise of this approach is that if the pattern of pressure delivery over a specified period (T) is different from the pattern over another specified period, the magnitude of the leak over said specified periods would also be different. In the presence of variability in pattern of pressure delivery, the statistical relation between the variable leak amount ($\Delta V$) or leak rate ($\Delta V/T$), on one hand, and the variable pattern of pressure delivery on the other hand will depend on the function that governs the relation between instantaneous pressure and instantaneous leak rate. Since leak amount or leak rate over specified periods can be measured or estimated, the problem resolves into selecting an appropriate index (or indices) that reflect(s) the breath-by-breath or time-to-time differences in pattern of pressure delivery. Thus, the fundamental approach is to establish the statistical relation between a variable $\Delta V$ or $\Delta V/T$ and one or more indices that reflect the variability in pattern of pressure delivery. Variability in the pattern of pressure delivery is often present spontaneously, particularly in non-invasive ventilation when patients are fairly alert. However, the ventilator can also deliberately impose variability in pattern of pressure delivery when spontaneous variability is minimal (for example, heavily sedated patients).

In accordance with one aspect of the present invention, there is provided a method for estimating gas leakage from the ventilator circuit and patient interface that relies on breath-by-breath or time-to-time variability in the pattern of pressure delivery by the ventilator, which comprises:

generating signals that correspond to pressure ($P_{CIRCUIT}$) and flow rate (Flow) in the ventilator circuit, integrating Flow (Integrated Flow), measuring the change in Integrated Flow ($\Delta V$) over an INTERVAL extending from a selected point in the expiratory phase of a ventilator cycle to a selected point during the expiratory phase of a nearby ventilator cycle, repeating said measurement of $\Delta V$ in at least two said INTERVALs, processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALs and the corresponding differences in said index or indices of $P_{CIRCUIT}$, and establishing from said relation the leak rate at specified $P_{CIRCUIT}$ values.

In accordance with a further aspect of the present invention, there is provided a device for estimating gas leakage from the ventilator circuit and patient interface that relies on breath-by-breath or time-to-time variability in the pattern of pressure delivery by the ventilator, which comprises:

computer for storing and processing data corresponding to pressure ($P_{CIRCUIT}$) and flow rate (Flow) in the ventilator circuit, with said processing comprising:

algorithm(s) for integrating Flow (Integrated Flow), algorithm(s) for measuring the change in Integrated Flow ($\Delta V$) over an INTERVAL extending from a selected point in the expiratory phase of a ventilator cycle to a selected point during the expiratory phase of a nearby ventilator cycle, repeating said measurement of $\Delta V$ in at least two said INTERVALs, algorithm(s) for processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALs and the corresponding differences in said index or indices of $P_{CIRCUIT}$, establishing from said relation the leak rate at specified $P_{CIRCUIT}$ values.

The method and system described above for estimating gas leakage may be embodied in one or more software applications comprising computer executable instructions executed by the processing structure. The software application(s) may comprise program modules including routines, programs, object components, data structures etc. and may be embodied as computer readable program code stored on a computer readable medium. The computer readable medium is any data storage device that can store data, which can thereafter be read by a processing structure. Examples of computer readable media include for example read-only memory, random-access memory, CD-ROMs, magnetic tape and optical data storage devices. The computer readable program code can also be distributed over a network including coupled computer systems so that the computer readable program code is stored and executed in a distributed fashion.

In accordance with an additional aspect of the present invention, there is provided a computer readable medium having a computer program stored thereon for estimating gas leakage from the ventilator circuit and patient interface that relies on breath-by-breath or time-to-time variability in the pattern of pressure delivery by the ventilator, the computer program comprising:

program code for receiving signals that correspond to pressure ($P_{CIRCUIT}$) and flow rate (Flow) in the ventilator circuit, program code for integrating Flow (Integrated Flow), program code for measuring the change in Integrated Flow ($\Delta V$) over an INTERVAL extending from a selected point in the expiratory phase of a ventilator cycle to a selected point during the expiratory phase of a nearby ventilator cycle, program code for repeating said measurement of $\Delta V$ in at least two said INTERVALs, program code for, based on $P_{CIRCUIT}$, producing an index or indices that reflect(s) the pattern of pressure delivery by the ventilator during each of said INTERVALs, program code for applying statistical methods to determine the relation between the differences in $\Delta V$ among INTERVALs and the corresponding differences in said index or indices of $P_{CIRCUIT}$, program code for establishing from said relation the leak rate at specified $P_{CIRCUIT}$ values.

In accordance with a further aspect of the present invention, there is provided a system for estimating gas leakage from the ventilator circuit and patient interface that relies on breath-by-breath or time-to-time variability in the pattern of pressure delivery by the ventilator, the system comprising:

a processing structure and a computer readable medium accessible by the processing structure for storing and processing data corresponding to pressure ($P_{CIRCUIT}$) and flow rate (Flow) in the ventilator circuit, wherein the processing is performed by integrating Flow (Integrated Flow), measuring the change in Integrated Flow ($\Delta V$) over an INTERVAL extending from a selected point in the expiratory phase of a ventilator cycle to a selected point during the expiratory phase of a nearby ventilator cycle, repeating said measurement of $\Delta V$ in at least two said INTERVALs, processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALs and the corresponding differences in said index or indices of $P_{CIRCUIT}$, and establishing from said relation the leak rate at specified $P_{CIRCUIT}$ values.

DETAILED DESCRIPTION OF THE INVENTION

Figure 1:
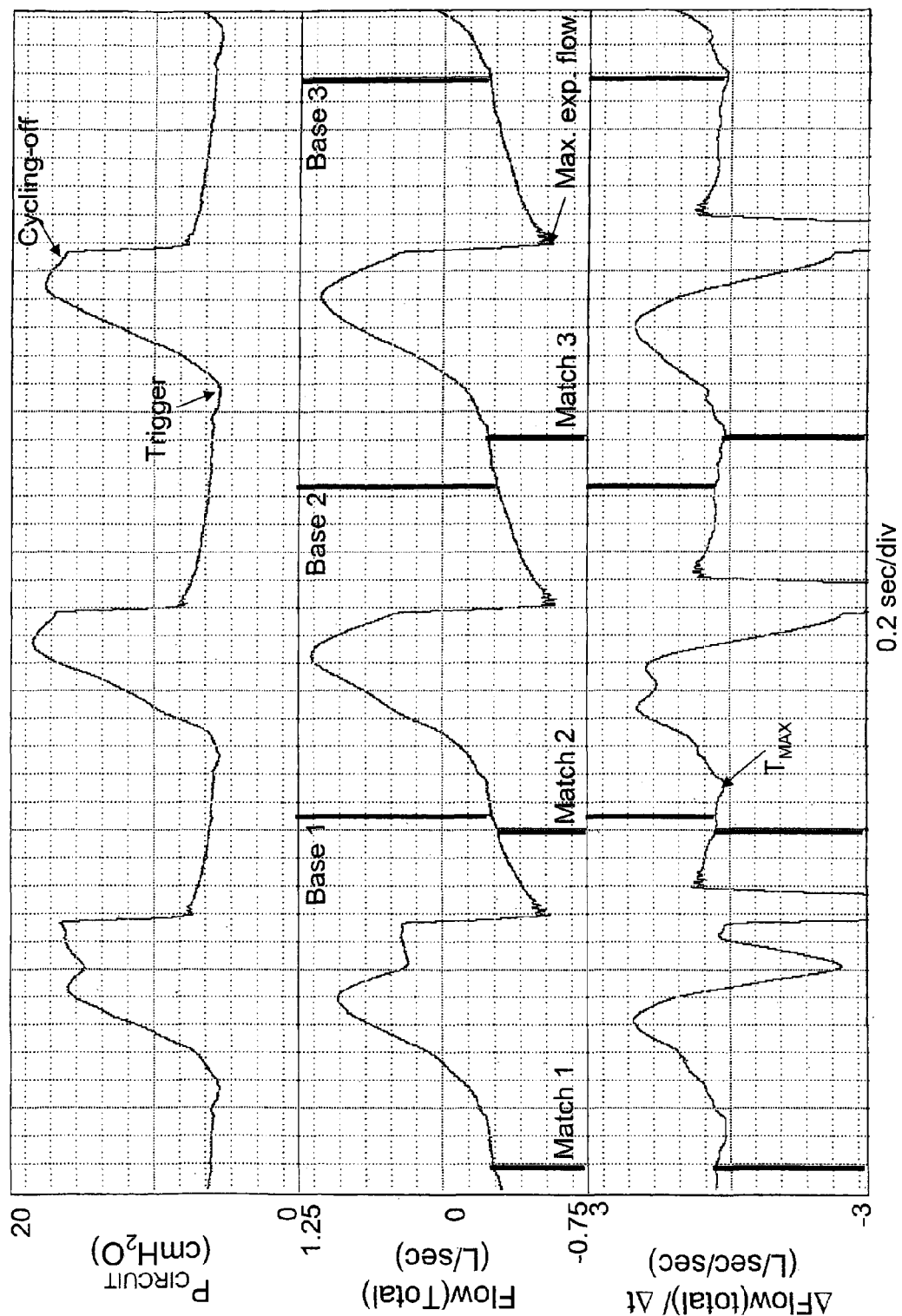
FIG. 1 contains graphical representations of circuit pressure, total flow (i.e. including leak) and the derivation of total flow in three consecutive breaths.

The present invention also incorporates steps to minimize the contribution of $\Delta V_{PATIENT}$ to the $\Delta V$ measured between two points, so that $\Delta V$ reflects more selectively the total leak between the two points. These steps will be discussed first because they represent desirable preliminary steps before the main invention is implemented.

1) Steps to Minimize the Contribution of $\Delta V_{PATIENT}$ to $\Delta V$:

At the end of the inflation phase (inspiration) the lung begins to empty and, given sufficient exhalation time before the next ventilator cycle is triggered, continues to do so until the neutral volume of the respiratory system (Functional Residual Capacity; FRC) is reached. At this point, flow rate of the air leaving the patient becomes zero and lung volume becomes constant. Under such conditions (i.e. sufficient exhalation time) the patient's end-expiratory volume does not differ from breath to breath (i.e. $\Delta V_{PATIENT}=0$) and any difference in volume (integrated flow rate) between the point of triggering of one breath (end-expiratory point) and the point of triggering of another breath is the result of leaks (i.e. $\Delta V=\Delta V_{LEAK}$). Thus, in such case, differences in $\Delta V$ values measured from the end-expiratory points of adjacent breaths provide a valid estimate of differences in leak during said adjacent breaths. Accordingly, when lung volume reaches FRC before triggering, lung volume near the triggering point can be selected to measure breath-by-breath variability in leak for the sake of correlating this with differences in pattern of applied pressure.

In patients who require mechanical ventilation the resistance to airflow is often high, thereby necessitating a longer exhalation time before FRC can be reached. To compound matters, these patients often breathe fast, with a short exhalation time. As result, the next breathing effort often begins before lung volume had reached FRC, a phenomenon called dynamic hyperinflation (DH). When this happens, there is no assurance that lung volume at the triggering point of one breath is the same as at the triggering point of another breath; the magnitude of DH can be very different from breath to breath depending on a host of factors. Thus, $\Delta V$ measured between end-expiratory points incorporates an undetermined component related to differences in DH. For example, assume that DH just before triggering in breath X was 0.3 liter and in breath Y was only 0.1 liter (for example, because of a longer exhalation phase or a smaller preceding tidal volume or an ineffective effort). The lung volume just before breath Y is 0.2 liter lower than lung volume before breath X. Assume further that total ΔV between the two points was 0.5 liter. In such a case assuming that the leak between the two points was 0.5 liter would result in an error of 0.2 liter since the measured ΔV is the net of leak volume plus difference in patient lung volume. It may be argued that since $\Delta V_{PATIENT}$ in successive breaths will cancel out over several breaths, it is reasonable to continue using the end-expiratory point for measuring ΔV for the sake of implementing the current invention. We have found, however, that although this may provide accurate results in some cases, considerable errors in leak estimation can result in other cases. The main reason for this is the fact that in situations associated with DH, the pattern of pressure application (the main independent variable in the current invention) not only influences leak magnitude ($\Delta V_{LEAK}$) but it also systematically influences the magnitude of DH (i.e. $\Delta V_{PATIENT}$). Thus, when the pressure pattern in one breath is such that a greater leak will result relative to another breath (for example, a longer inflation phase, or higher pressure and, hence, tidal volume during the inflation phase), not only will $\Delta V_{LEAK}$ be greater but DH will also tend to be higher at the end of this breath (because of the relatively shorter exhalation time or larger associated tidal volume). When both components of ΔV change in the same direction in response to changes in pattern of applied pressure, systematic errors can result in leak estimation. Accordingly, while one may accept some error and use the end-expiratory points to measure ΔV, it is desirable to implement steps that minimize the contribution of $\Delta V_{PATIENT}$ to ΔV. There are several approaches to doing that:

A) One may continue to use the end-expiratory points to measure ΔV, but incorporate one or more independent variables, which are known to affect DH, in the regression between ΔV and the index(es) of pressure pattern. For example, in a setting that promotes DH, the magnitude of DH is affected by the duration of the expiratory phase. Accordingly one may design the regression analysis to include expiratory time (interval from cycling off to next trigger; $T_E$) as an additional independent variable in the regression between ΔV and the index(es) of pressure pattern. Other variables that may affect DH may also be added (see C and D below). I believe this approach is quite effective but not as effective as the other approaches described below. The main weakness of approach A is that one must either assume a linear relation between lung volume and the independent variable(s) used (i.e. $T_E$ in this case), which is not particularly accurate, or apply non-linear regression analysis for said relation(s) and this is quite a complex and challenging task. One may, however, use this approach if one is willing to accept a certain level of inaccuracy in leak estimation.

B) Another approach is to select the points at which ΔV is measured so that they are equidistant in time from the cycling off point of the preceding inflation phase. This would correct for the impact of differences in $T_E$ on DH but leaves the effect of other variables unaccounted for. Thus, this approach represents a partial solution to the problem. It may, however, be used when the need for accuracy is not so stringent.

C) A preferable approach, and which is used in the preferred embodiment, is to select the points at which ΔV is measured so that they are closely matched in the values of flow rate and the derivative of flow rate (ΔFlow/Δt). The rationale for this approach is that, unless resistance to flow is different, when expiratory flow rate is the same at the two points, alveolar pressure ($P_{ALV}$) is also the same. Important differences in resistance between two nearby expiratory points having the same flow rate are extremely unlikely. Thus, selecting two points, one before and one after an inflation phase, that have the same expiratory flow rate essentially ensures a similar $P_{ALV}$. $P_{ALV}$ during expiration is primarily a function of lung volume, as governed by the pressure-volume relation of the passive respiratory system. Thus, if the points selected have the same $P_{ALV}$, they will also have the same lung volume except in the presence of factors that alter the relation between lung volume and $P_{ALV}$. These factors are well known and can be accounted for. Thus, the relation between lung volume and flow rate can be altered in the presence of noise in the flow signal (for example, secretions, cardiac artifacts). These can be neutralized by appropriate filtering of the flow signal or by avoiding regions in which the flow signal is noisy. Presence of expiratory or inspiratory muscle activity can result in a higher or lower $P_{ALV}$, respectively, and hence different expiratory flow rate, at the same volume. But, under these circumstances, the rate of change in flow rate (ΔFlow/Δt) should be different even though flow rate is the same. For this reason, in the current approach the points are selected to have similar ΔFlow/Δt as well as similar flow rate.

FIG. 1 shows the approach preferably used for selecting the points in time at which to calculate ΔV. This Figure shows the circuit pressure, total flow rate (i.e. including leak) and the derivative of total flow rate in three consecutive breaths. To reduce noise, the flow tracing is the 100 msec moving average of the original flow rate and the flow derivative was obtained with a 200 msec smoothing interval. Clearly, other filtering techniques can be used.

The first step in this approach is to define the search region (during the various expiratory phases) in which to look for points with matching Flow rate and ΔFlow/Δt. It can be seen that during the expiratory phase (negative flow rate) ΔFlow/Δt declines monotonically and flow rate rises monotonically (i.e. the two signals are moving in opposite directions), until a few hundred milliseconds before ventilator triggering where ΔFlow/Δt begins to rise again and both flow rate and its derivative are now moving in the same direction (i.e. up). This secondary rising phase, with concurrent increase in both signals, marks the beginning of inspiratory muscle activity. Thus, points to the right of the trough in ΔFlow/Δt are avoided since the relation between lung volume and $P_{ALV}$ in this region does not follow the passive relation. The point at which ΔFlow/Δt is lowest in this pre-inspiratory region [for example, Trigger time to Trigger time−0.5 sec] accordingly defines the end of the search region for matching points ($T_{MAX}$). The beginning of the search region in each breath is defined arbitrarily as 200 msec after the point of maximum expiratory flow rate, which usually occurs soon after the cycling off point (FIG. 1).

In the preferred embodiment, the search regions in two consecutive expiratory phases are searched for points where both flow rate values are within 0.01 L/sec of each other and both ΔFlow/Δt values are within 0.1 L/sec/sec of each other. An additional condition is that the flow rate signal should be free of significant noise at both points. The search begins from $T_{MAX}$ and proceeds backward until a match is found. The later of the two matched points is referred to as the Base Point and the matching point in the preceding breath is referred to as Match Point (FIG. 1).

At times, a matching point cannot be found in the immediately preceding breath. In this case the search for a match point is done in the ventilator cycle 2 cycles before the base point and, if no match is found, the search is done in the ventilator cycle 3 cycles before the base point. Thus the interval between the base and the corresponding match point may contain up to three ventilator cycles. Inclusion of more than three cycles in a given interval is not beneficial as it smoothes out the breath-by-breath variability in pattern of pressure delivery, the main independent variable. In the remainder of this document, the term INTERVAL will be used to indicate the region between a base and a corresponding match point, which typically contains only one ventilator cycle but may contain up to three.

Once the base-match pairs are identified, the difference in integrated flow between the two points in each pair is calculated, providing $\Delta V$. $\Delta V$ is measured across a plurality of INTERVALs. This is the main dependent variable which will be statistically related to the index(es) reflecting the pattern of pressure delivery.

D) A further optional improvement on the method described in C) above is to include additional variables that may affect the relation between lung volume and $P_{ALV}$ in the regression between $\Delta V$ and the pressure index(es). I have found that when $\Delta V$ is measured at points of similar flow rate and $\Delta Flow/\Delta t$, the values obtained in the complete absence of leaks is not always zero, indicating that a certain $\Delta V_{PATIENT}$ may still exist even when $\Delta V$ is measured between points of nearly equal flow rate and $\Delta Flow/\Delta t$. Although this residual $\Delta V_{PATIENT}$ is typically very small, it is desirable to account for it, particularly if computational time is not an issue. The most likely reason for this residual $\Delta V_{PATIENT}$ is the viscoelastic behavior of the lung, which affects the relation between lung volume and $P_{ALV}$. Thus, because of the time dependent phenomena of stress relaxation and stress recovery, and associated changes in surfactant levels, lung volume at a given $P_{ALV}$ is higher the closer the point of measurement is to the end of the inflation phase and the longer the duration of the preceding inflation phase. Thus, I devised a number of measurements that could alter the relation between lung volume and $P_{ALV}$ and demonstrated that they indeed correlate with the residual $\Delta V_{PATIENT}$. Those that significantly impact the residual $\Delta V_{PATIENT}$ in some patients include:

1) "dmatch delta": Time difference between the measurement point (Base or Match) and the end of the preceding inflation phase: Accordingly, the time difference between the base point and the preceding cycling-off time is measured ($\Delta$base). Likewise, the time difference between the match point and the end of the preceding inflation phase is measured ($\Delta$match). Differences between these two values could alter the relation between lung volume and $P_{ALV}$ at the two points. Thus, [$\Delta$base−$\Delta$match] is calculated for each pair. Because the effect of this difference decreases as the time from the end of inflation phase increases, the difference is further divided by the average of the two values: "dmatch delta"=[($\Delta$base−$\Delta$match)/0.5($\Delta$base+$\Delta$match)]. This variable is then optionally used as an independent variable in the regression.

2) $dT_{HIGH}$: Difference between the durations of the inflation phases preceding the base and match points: The time difference between trigger and cycling-off time of the inflation phase preceding the base point is calculated ($T_{HIGH}$Base). The same time difference is also calculated for the inflation phase preceding the match point ($T_{HIGH}$Match). The difference between the two values is calculated ($dT_{HIGH}$) for each base-match pair, and the resulting values are optionally used as an additional independent variable in the regression.

3) $T_{INTERVAL}$−average $T_{INTERVAL}$: I have also found that in some cases $\Delta V_{PATIENT}$ is affected by the interval between base and match points (i.e. $T_{INTERVAL}$). Accordingly, another optional independent variable is calculated from current $T_{INTERVAL}$ minus the average of all $T_{INTERVAL}$ values used in the regression.

4) Although flow rate and $\Delta Flow/\Delta t$ the base and match points are, by design, very close, they may not be exactly the same due to the digital nature of the data. Accordingly, to account for any small differences that may exist, the actual difference between flow rate at base point and flow rate at match point is calculated for all base-match pairs: dFlow=flow rate at base point−flow rate at match point. Likewise the difference in $\Delta Flow/\Delta t$ is calculated: ddflow/dt=$\Delta Flow/\Delta t$ base point−$\Delta Flow/\Delta t$ match point. These two variables (dFlow and ddflow/dt) may also be used in the regression as independent variables.

All these variables that are intended to minimize the contribution of $\Delta V_{PATIENT}$ to $\Delta V$ (1 to 4 above) may be used in their actual values or after normalization by dividing by $T_{INTERVAL}$. If the actual value of the dependent variable is used (i.e. $\Delta V$, in liters), then all the independent variables are used as actual values. On the other hand, when the dependent variable is normalized by dividing it by $T_{INTERVAL}$ (i.e. $\Delta V/T_{INTERVAL}$, in L/sec), then all the independent variables are similarly normalized. In the preferred embodiment the dependent and independent variables are divided by $T_{INTERVAL}$.

2) Calculation of Index(es) that Reflect the Pattern of Pressure Delivery:

During mechanical ventilation there is a baseline pressure that is delivered during expiration (PEEP). This typically varies between 0 and 20 cmH$_2$O. When the ventilator senses a patient effort, it raises the pressure above PEEP. This step is called triggering. This phase of raised pressure (high pressure phase; $T_{HIGH}$) lasts until the ventilator is instructed to cycle-off, at which point the pressure is returned to PEEP. The event that triggers cycling-off varies depending on the ventilation mode used. But, regardless of what cycles off the ventilator, within each cycle there is a high-pressure phase of duration $T_{HIGH}$, and a low-pressure phase of duration $T_{LOW}$. The proposed approach takes advantage of the fact that $T_{HIGH}$ and $T_{LOW}$ vary, or can be made to vary, from breath to breath or from time to time. Variability in the pressure reached during $T_{HIGH}$, as occurs during some ventilation modes (for example, PAV, volume-cycled ventilation), can also be put to use to establish the relation between instantaneous pressure and instantaneous leak.

Figure 2:
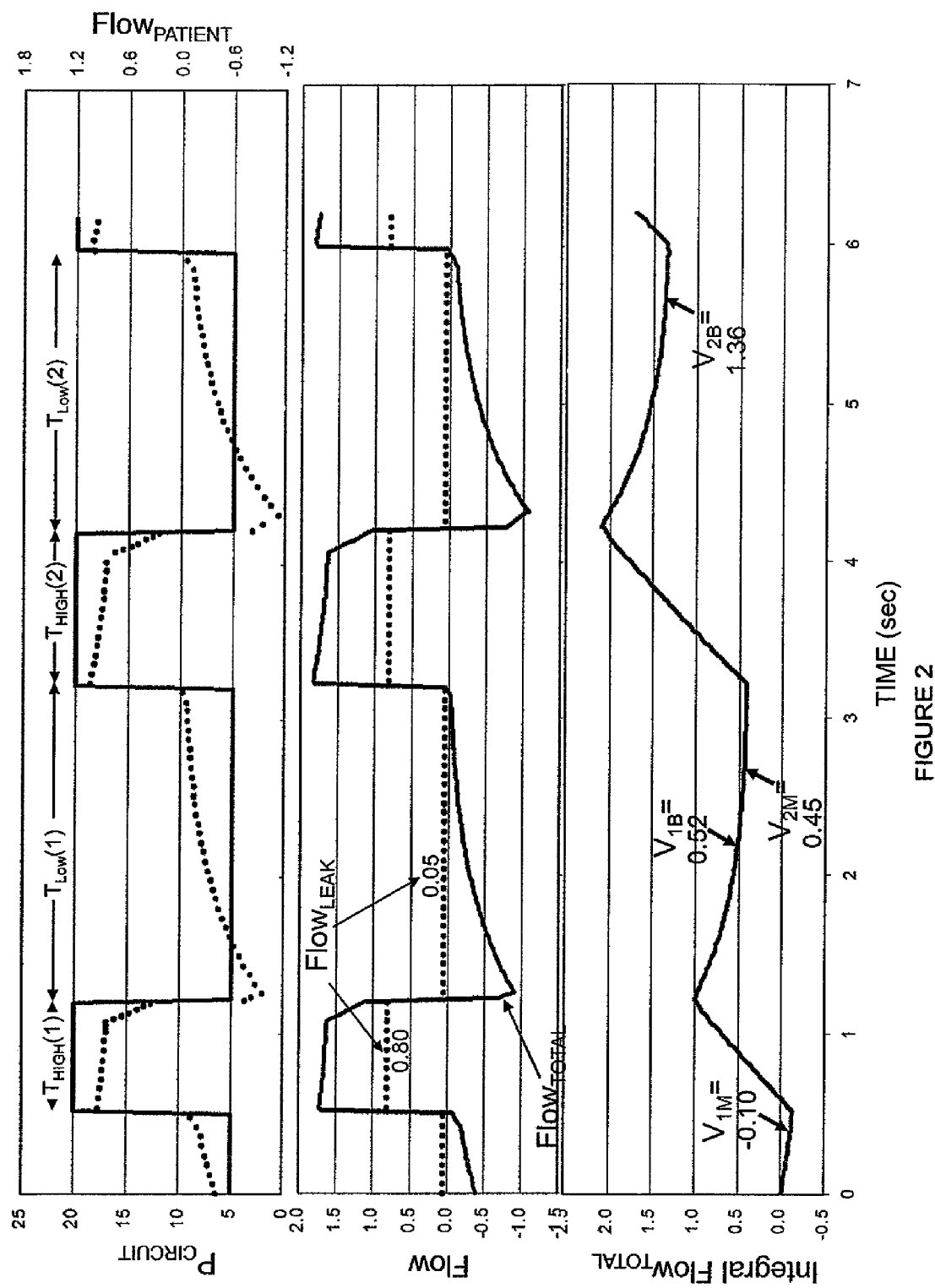
FIG. 2 contains graphical representations illustrating how variability in $T_{HIGH}$ and $T_{LOW}$ can be used to advantage to estimate leak levels at different circuit pressures.

FIG. 2 illustrates how variability in $T_{HIGH}$ and $T_{LOW}$ can be used to advantage to estimate leak levels at different circuit pressures. This Figure is a simulation that illustrates the simplest application of the proposed approach, where circuit pressure rises and falls in a square fashion during the ventilator cycle and the high and low pressures are the same in all INTERVALs. Application in more complex situations will be described later. The Figure illustrates two breaths in which PEEP is 5 cmH$_2$O and pressure rises to 20 cmH$_2$O during the inspiratory phase. $T_{HIGH}$ was 0.7 and 1.0 second, respectively, in the two breaths (see Table 1 below). True patient flow rate is shown in the top panel (dotted line). In this simulation a hypothetical leak was selected having the following function [leak=(P−4)*0.05]. Thus, $P_{THRESH}$ is 4 cmH$_2$O and the relation above this threshold is linear with a slope of 0.05 L/sec/cmH$_2$O. This function results in a leak of 0.05 L/sec during $T_{LOW}$ (P=5) and a leak of 0.80 L/sec during $T_{HIGH}$ (P=20), as illustrated by the dotted line of the middle panel (FIG. 2). The flow rate measured by the ventilator (Flow$_{TOTAL}$) is the sum of patient flow rate (dotted line, top panel) and leak flow rate (dotted line, middle panel), and is shown as the solid line in the middle panel. The bottom panel shows the integral of total flow rate, which, consistent with the presence of a leak, is drifting upwards. The ventilator has no information about the type or mathematical constants of the leak or about true patient flow rate. For each ventilator cycle (breath) two points are selected, one before and one after the high-pressure phase ($V_{1M}$ and $V_{1B}$ for breath one and $V_{2M}$ and $V_{2B}$ for breath two, bottom panel, FIG. 2). These points correspond to the match and base points described in section 1 above (FIG. 1).

TABLE 1

|  | INT. 1 | INT. 2 |
|---|---|---|
| ΔV | 0.62 | 0.91 |
| $T_{HIGH}$ | 0.70 | 1.00 |
| $T_{INTERVAL}$ | 1.84 | 3.18 |
| $T_{LOW}$ | 1.14 | 2.18 |
| $T_{HIGH}/T_{INTERVAL}$ | 0.38 | 0.31 |
| $T_{LOW}/T_{INTERVAL}$ | 0.62 | 0.69 |
| $\Delta V/T_{INTERVAL}$ | 0.34 | 0.29 |

It is clear that the volume difference between the point after and the point before each $T_{HIGH}$ is related to the time spent in $T_{HIGH}$ and the time spent in $T_{LOW}$. Thus:

For INTERVAL 1: $\Delta V(1) = K_{HIGH} * T_{HIGH}(1) + K_{LOW} * T_{LOW}(1)$ AND For INTERVAL 2: $\Delta V(2) = K_{HIGH} * T_{HIGH}(2) + K_{LOW} * T_{LOW}(2)$ where $K_{HIGH}$ and $K_{LOW}$ are the leak rates during $T_{HIGH}$ and $T_{LOW}$, respectively. It can be seen that there are now two different equations with only two unknown constants, $K_{HIGH}$ and $K_{LOW}$. Solving for these two constants (using the data in Table 1) yields a $K_{HIGH}$ of 0.798 and a $K_{LOW}$ of 0.054, almost identical to the actual leak. These values can then be plotted against the corresponding pressures (20 and 5, respectively). Of course, in this case the exact function of the leak cannot be determined (i.e. leak levels between the two pressure values cannot be estimated). However, in this case such information is not needed since virtually all the time is spent at these two pressures. Thus, estimated leak level would simply jump up to 0.798 at triggering and down to 0.054 at cycling off.

It is important to note that simple, proportional differences between the two INTERVALs in their $T_{HIGH}$ and $T_{LOW}$ is not sufficient to solve for $K_{HIGH}$ and $K_{LOW}$. For example, it would not be possible to solve for $K_{HIGH}$ and $K_{LOW}$ if $T_{HIGH}(2)$ were twice $T_{HIGH}(1)$ and $T_{LOW}(2)$ were twice $T_{LOW}(1)$. For these constants to be estimated it is necessary that the fractions of total time ($T_{INTERVAL}$) spent in the high and low range be different. In Table 1 it can be seen that $T_{HIGH}/T_{INTERVAL}$ was 0.38 and 0.31, respectively for INTERVALs 1 and 2, while $T_{LOW}/T_{INTERVAL}$ was 0.62 and 0.69, respectively. Thus, a critical requirement for this simplified approach to work is the presence of some breath-by-breath variability in $T_{HIGH}/T_{INTERVAL}$ and, by extension, in $T_{LOW}/T_{INTERVAL}$. In assisted modes of ventilation (for example, pressure support ventilation (PSV), proportional assist ventilation (PAV)) enough variability typically occurs spontaneously due to natural differences in the duration of patient inspiratory efforts. In assisted volume-cycled ventilation $T_{HIGH}$ does not vary between breaths but $T_{INTERVAL}$ varies spontaneously, so that differences in $T_{HIGH}/T_{INTERVAL}$ still occur. Under some circumstances, for example during controlled ventilation or when the patient is heavily sedated, there may not be enough differences in $T_{HIGH}/T_{INTERVAL}$ between breaths. Such an occurrence can, however, be readily detected by the ventilator (for example, by monitoring standard deviation of $T_{HIGH}/T_{INTERVAL}$) and measures can then be taken to force such differences. For example, in PSV and PAV cycling off can be advanced or delayed deliberately in some breaths while in volume-cycled ventilation cycle duration or ventilator inspiratory time can be altered in some breaths. The example given here (FIG. 2 and Table 1) shows that relatively small differences in $T_{HIGH}/T_{INTERVAL}$ (0.07 in this case) can produce satisfactory results even when only two breaths are used to estimate the leak.

The following two equations are the same as the above equations except that all terms in each equation were divided by the respective $T_{INTERVAL}$:

For INTERVAL 1: $\Delta V(1)/T_{INTERVAL}(1) = K_{HIGH} * [T_{HIGH}(1)/T_{INTERVAL}(1)] + K_{LOW} * [T_{LOW}(1)/T_{INTERVAL}(1)]$ and, For INTERVAL 2: $\Delta V(2)/T_{INTERVAL}(2) = K_{HIGH} * [T_{HIGH}(2)/T_{INTERVAL}(2)] + K_{LOW} * [T_{LOW}(2)/T_{INTERVAL}(2)]$ The corresponding $T_{INTERVAL}$-normalized values are shown at the bottom of Table 1. It is mathematically obvious that the estimates of $K_{HIGH}$ and $K_{LOW}$ would be identical. Thus, estimates of leak using the proposed approach can be made using either the raw or $T_{INTERVAL}$-normalized values of $\Delta V$, $T_{HIGH}$ and $T_{LOW}$.

The above example represents the operation of the proposed method under idealized conditions and is intended only to illustrate the basic principles of this method. In practice, pressure does not rise and fall in a square fashion and, at least in some ventilation modes (for example, PAV, volume cycled ventilation) pressure does not rise to the same level with each ventilator cycle. There are several ways to apply the current invention under these conditions. All share the common approach of utilizing breath-by-breath variability in pattern of pressure delivery to estimate the relation between instantaneous leak and instantaneous pressure. The following are four examples of how the proposed approach can be implemented under conditions of non-square and/or non-constant pressure waveforms. Other methods of implementation are also possible. It is obvious that all such approaches require a minimum of two ventilator cycles to obtain leak estimates.

A) Converting the Pressure Waveform in Individual INTERVALs into Two Square Functions of Time with the High and Low Pressures being Constant Across INTERVALs.

Figure 3:
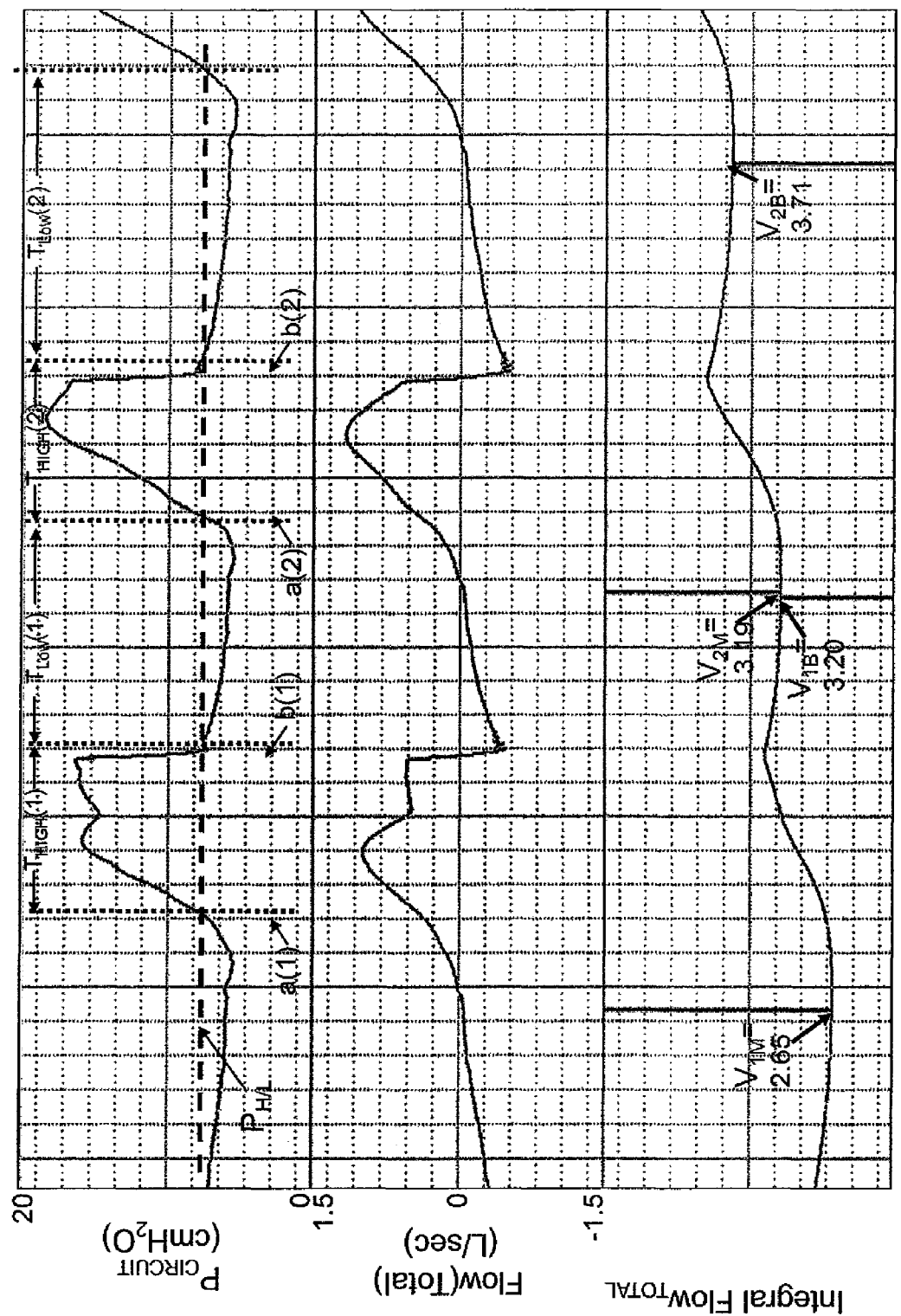
FIG. 3 contains graphical representations of two breaths with very different profiles.

This approach attempts to reproduce the idealized situation described above (as in FIG. 2). FIG. 3 illustrates two breaths with very different pressure profiles. $\Delta V(1)$ and $\Delta V(2)$ are measured from differences in integrated flow at base ($Vi_B$) and match ($Vi_M$) points, as described in section 1 above. Thus, $\Delta V(1) = V_{1B} - V_{1M}$, and $\Delta V(2) = V_{2B} - V_{2M}$ (bottom tracing, FIG. 3). An arbitrary pressure level is selected that roughly separates the high and low-pressure phases ($P_{H/L}$). The exact location of this level is not critical. In one embodiment, this $P_{H/L}$ is selected as the level of positive end expiratory pressure (PEEP) plus a specified small value (for example, 2 to 3 cmH$_2$O). In this case, a pressure of 8 cmH$_2$O was selected (horizontal dashed line, top panel FIG. 3). Next, the times at which pressure crosses this level on the way up (a(i)) and on the way down (b(i)) are identified (vertical dotted lines, top panel, FIG. 3). The time difference between the two vertical lines is measured in each breath, producing preliminary values of $T_{HIGH}(1)$ and $T_{HIGH}(2)$. $T_{INTERVAL}(1)$ and $T_{INTERVAL}(2)$ are measured from the time difference between the selected expiratory points ($T_{INTERVAL}(1)$=time of $V_{1B}$–time of $V_{1M}$, ... etc). $T_{LOW}$ is then calculated from the respective differences between $T_{INTERVAL}$ and $T_{HIGH}$ ($T_{LOW}(1)$ and $T_{LOW}(2)$). Next, for each INTERVAL the integral of pressure during $T_{HIGH}$ is calculated ($\Sigma(P_{HIGH} \cdot dt)$). The integral of pressure across $T_{INTERVAL}$ is also calculated ($\Sigma(P_{INTERVAL} \cdot dt)$). The integral of pressure during $T_{LOW}$ (i.e. $\Sigma(P_{LOW} \cdot dt)$) is calculated from: $\Sigma(P_{INTERVAL} \cdot dt) - \Sigma(P_{HIGH} \cdot dt)$. A reference high pressure ($P_{HIGH}REF$) and a reference low pressure ($P_{LOW}REF$) are selected. $P_{HIGH}REF$ can be selected according to any of several formulas that take variability in the high pressure into account. A suitable formula for selecting $P_{HIGH}REF$ is the average of peak pressures in the ventilator cycles being analyzed, but other treatments may also be suitable (for example, 0.7*average peak pressure or average of average high pressure in the different breaths). In the example illustrated in FIG. 3, a $P_{HIGH}REF$ of 17.5 was selected, this being the average of the peak pressures in the two breaths. A suitable $P_{LOW}REF$ can be any value that is common to all INTERVALS during $T_{LOW}$, but other selections may also be reasonable (for example, average of pressure values at a specific time during expiration). In the example of FIG. 3, a $P_{LOW}REF$ of 6 cmH$_2$O was selected, this being the average of the two pressures at $V_{1B}$ and $V_{2B}$. $T_{HIGH}$ is then recalculated for each INTERVAL to produce a normalized $T_{HIGH}$. This is the time which, when multiplied by $P_{HIGH}REF$ gives the same $\Sigma(P_{HIGH} \cdot dt)$. Thus, normalized $T_{HIGH}(1)$ and $T_{HIGH}(2)$ are given by:

normalized $T_{HIGH}(1) = \Sigma(P_{HIGH}(1) \cdot dt)/P_{HIGH}REF$ and normalized $T_{HIGH}(2) = \Sigma(P_{HIGH}(2) \cdot dt)/P_{HIGH}REF$ The same is done for the low-pressure phase to calculate the normalized $T_{LOW}$, the $T_{LOW}$ that would produce the same $\Sigma(P_{LOW} \cdot dt)$ at $P_{LOW}REF$. Thus:

normalized $T_{LOW}(1) = \Sigma(P_{LOW}(1) \cdot dt)/P_{LOW}REF$ and normalized $T_{LOW}(2) = \Sigma(P_{LOW}(2) \cdot dt)/P_{LOW}REF$ A normalized $T_{INTERVAL}$ is then calculated for each interval. Thus:

normalized $T_{INTERVAL}(1)$ = normalized $T_{HIGH}(1)$ + normalized $T_{LOW}(1)$ and normalized $T_{INTERVAL}(2)$ = normalized $T_{HIGH}(2)$ + normalized $T_{LOW}(2)$ Finally, normalized $T_{HIGH}/T_{INTERVAL}$ is calculated for each INTERVAL. Thus:

Normalized $T_{HIGH}/T_{INTERVAL}(1)$ = normalized $T_{HIGH}(1)$/normalized $T_{INTERVAL}(1)$ and Normalized $T_{HIGH}/T_{INTERVAL}(2)$ = normalized $T_{HIGH}(2)$/normalized $T_{INTERVAL}(2)$ The different $\Delta V$ levels are normalized by dividing by $T_{INTERVAL}$.

The leak levels at $P_{HIGH}REF$ and $P_{LOW}REF$ can then be calculated as was described for the idealized situation described above. Thus:

Normalized $\Delta V(1) = K_{HIGH}$*normalized $T_{HIGH}(1)$ + $K_{LOW}$*normalized $T_{LOW}(1)$ and Normalized $\Delta V(2) = K_{HIGH}$*normalized $T_{HIGH}(2)$ + $K_{LOW}$*normalized $T_{LOW}(2)$ Since all values in these two equations are known except for $K_{HIGH}$ and $K_{LOW}$, these values can be computed from an examination of the data of two INTERVALs. Thus, $K_{HIGH} = (\Delta V(2) - (\Delta V(1)*\text{Norm } T_{LOW}(2)/\text{Norm } T_{LOW}(1)))/(\text{Norm } T_{HIGH}2 - (\text{Norm } T_{HIGH}(1)*\text{Norm } T_{LOW}(2)/\text{Norm } T_{LOW}(1)))$ AND, $K_{LOW} = (\Delta V(1) - (K_{HIGH}*\text{Norm } T_{HIGH}(1)))/(\text{Norm } T_{LOW}(1))$ Also, as discussed earlier, the same results should be obtained if all $\Delta V$ and time values in the above equations are divided by the respective normalized $T_{INTERVAL}$.

Figure 4:
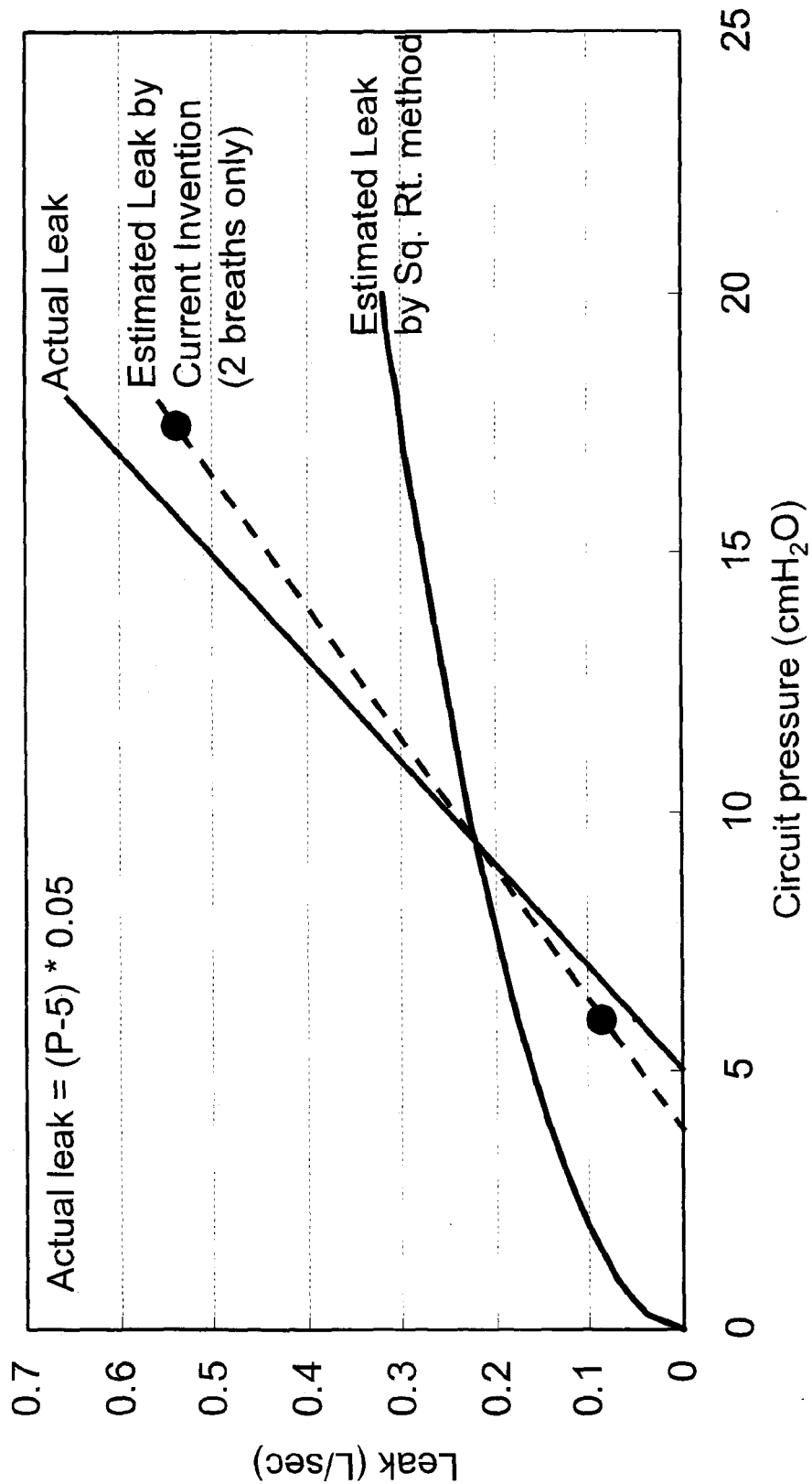
FIG. 4 contains graphical representations of a plot of actual leak and estimate leak values determined by the method of the invention and the square root method of the prior art.

As discussed in the case of the idealized situation, the normalized $T_{HIGH}/T_{INTERVAL}$ values of the two (or more) INTERVALs must be different from each other in order to be able to solve the equations for $K_{HIGH}$ and $K_{LOW}$. In the case of the two INTERVALs shown in FIG. 3, the normalized $T_{HIGH}/T_{INTERVAL}$ values were 0.33 and 0.27, respectively. Other relevant values are shown in Table 2 below. Inserting these values in the above equations yields a $K_{HIGH}$ of 0.535 and a $K_{LOW}$ of 0.083. Solid dots in FIG. 4 show these values plotted against $P_{HIGH}REF$ and $P_{LOW}REF$ (17.5 and 6.0 respectively). The straight diagonal line describes the actual leak in effect (Leak=(P−5)*0.05). It can be seen that leak estimates using this approach were quite reasonable considering that only two INTERVALs were used. Thus, this method detected the presence of a pressure intercept ($P_{THRESH}$), which was only slightly lower than the actual value (4 instead of 5) and the leak estimates at the two selected pressures were only slightly different from the actual values. Despite these errors, the results represent a substantial improvement over assuming that the leak follows the relation obtained with fixed orifices (Leak=K*P$^{0.5}$), as recommended in the prior art (U.S. Pat. No. 5,803,065). Application of the latter equation in this case yields the relation given by the curved line in FIG. 4. The same results could be obtained if a linear regression is performed on these two data sets with $\Delta V/T_{INTERVAL}$ as the dependent variable and normalized $T_{HIGH}/T_{INTERVAL}$ as the independent variable. With such treatment the intercept of the relation is $K_{LOW}$ and the sum of the slope and intercept is $K_{HIGH}$.

TABLE 2

|  | INT. 1 | INT. 2 |
| --- | --- | --- |
| $\Delta V$ | 0.540 | 0.522 |
| Norm. $T_{HIGH}$ | 0.77 | 0.69 |
| Norm. $T_{INTERVAL}$ | 2.32 | 2.54 |
| Norm. $T_{LOW}$ | 1.55 | 1.85 |
| Norm. $T_{HIGH}/T_{INTERVAL}$ | 0.331 | 0.270 |
| Norm. $T_{LOW}/T_{INTERVAL}$ | 0.669 | 0.730 |
| $\Delta V/T_{INTERVAL}$ | 0.233 | 0.206 |

The main disadvantages of this method of implementing the current invention (i.e. current algorithm) are that: a) it provides leak estimates at only two pressure levels, so that leak levels at intermediate pressure levels or at pressures >$P_{HIGH}REF$ can only be inferred by assuming a mathematical function that passes through these two points. b) The estimate of leak at $P_{HIGH}REF$ and $P_{LOW}REF$ is only approximate (for Example, FIG. 4) because there is the assumption that leak is proportional to pressure in the pressure range that is being averaged within $T_{HIGH}$ and $T_{LOW}$. Its main advantage, however, is that it requires only two INTERVALs to arrive at reasonable estimates of the leak at two pressure points, one low and one high. Thus, it is particularly suitable at the initiation of mechanical ventilation or upon detecting a change in the leak. When multiple INTERVALs are available, other algorithms become preferable (see below). Nonetheless, the same implementation (converting the pressure waveform into two square functions of time with the high and low pressures being constant across INTERVALs) can be used on multiple ventilator cycles by measuring $\Delta V$ across a plurality INTERVALs, selecting suitable $P_{HIGH}REF$ and $P_{LOW}REF$ values and calculating normalized $T_{HIGH}$ and $T_{LOW}$ for each INTERVAL. The $K_{HIGH}$ and $K_{LOW}$ values can then be obtained by regression analysis where $\Delta V$ is the dependent variable and normalized $T_{HIGH}$ and $T_{LOW}$, as well as the variables that minimize $\Delta V_{PATIENT}$ (see section 1 above), are the independent variables. Alternatively, if $\Delta V/T_{INTERVAL}$ were to be used as the dependent variable, a simple regression of $\Delta V/T_{INTERVAL}$ vs. normalized $T_{HIGH}/T_{INTERVAL}$, along with the variables that minimize $\Delta V_{PATIENT}$ would be adequate. In this case, the intercept would be $K_{LOW}$ and the sum of intercept and the coefficient of $T_{HIGH}/T_{INTERVAL}$ is $K_{HIGH}$. Where peak pressure is constant (for example, pressure support ventilation), and particularly when the rise time during $P_{HIGH}$ is short, this method of implementation provides excellent results since the pressure profile is close to being square and of fixed amplitude, as in the idealized situation. The more the actual pressure profile deviates from the idealized situation the less reliable this approach is, although it continues to yield better results than assuming a priori a specific function, when the actual relation is different from the assumed function (for example, FIG. 4).

A particularly advantageous approach is to employ this method of implementation at the beginning of mechanical ventilation, or upon detecting a change in leak, and to switch to more precise methods of implementation as more INTERVALs accumulate. Thus, in one aspect of the present invention, leak level is monitored, for example from average flow rate over a plurality of ventilator cycles. A change in leak is identified when said average flow rate signal increases or decreases significantly. Alternately, a change in leak is identified if one or more recent $\Delta V$ values deviate significantly from what is expected based on estimates of the leak made from a plurality of previous INTERVALs. Once a change in leak is detected, the ventilator insures that the first few breaths that follow contain sufficient variability in the $T_{HIGH}/T_{INTERVAL}$ ratio. This can be done in a variety of ways depending on the ventilation mode in use. The current method of implementation is then employed utilizing these early cycles to rapidly reach an approximate estimate of the new leak. As more INTERVALs accumulate a different algorithm is used that provides a more precise definition of the leak function.

B) Stratifying Ventilator Cycles According to Pressure Levels during the High-pressure Phase:

This algorithm is suitable when the amplitude of delivered pressure varies among different ventilator cycles. Here, as with the previous algorithm, high and low pressure zones are separated, and preliminary $T_{HIGH}$ and $T_{LOW}$ values are calculated for each of the available INTERVALs. A $P_{LOW}REF$ is also selected and a normalized $T_{LOW}$ is calculated. So far, these steps are similar to algorithm A and the same approach proposed in algorithm A may be used to implement these steps. Average pressure during $T_{HIGH}$ (i.e. average $P_{HIGH}$) is calculated for each INTERVAL from $(\Sigma(P_{HIGH}\cdot dt))/$preliminary $T_{HIGH}$. The available INTERVALs are then stratified according to their average $P_{HIGH}$ to generate two or more groups of roughly equal numbers. For example, 6 INTERVALs may have an average $P_{HIGH}$ between 8 and 11.5 cmH$_2$O, another 7 may have an average $P_{HIGH}$ between 11.5 and 13.3 cmH$_2$O and another 5 INTERVALs have average $P_{HIGH}>13.3$ cmH$_2$O. These groups may be conveniently referred to as $G_{HIGH}1$, $G_{HIGH}2$, and $G_{HIGH}3$. The average of average $P_{HIGH}$ values within each group is calculated and used as a $P_{HIGH}REF$ for members of the group. A normalized $T_{HIGH}$ for each INTERVAL within a given group is calculated from: $(\Sigma(P_{HIGH}\cdot dt)$ for that INTERVAL/$P_{HIGH}REF$ of the group to which this INTERVAL belongs). As with the previous algorithm, $\Delta V$ is measured from differences in integrated flow at base and match points that are selected to minimize the contribution of $\Delta V_{PATIENT}$ to overall $\Delta V$ (section 1). The results can be tabulated as in Table 3 below. Each base-match interval occupies a row. For each INTERVAL, $\Delta V$, the dependent variable, is listed along with the corresponding normalized $T_{LOW}$. $T_{HIGH}$ for the INTERVAL is positioned in the appropriate column depending on which group the INTERVAL belongs to. Empty cells are populated with zeroes. This creates four independent variables for each $\Delta V$. Additional variables may be added to minimize the contribution of $\Delta V_{PATIENT}$ to $\Delta V$ (section 1). A regression analysis can then be performed which will generate a coefficient for each of the time variables (Table 4 below). This coefficient represents the leakage rate at the relevant $P_{REFERENCE}$. Thus, the results of regression analysis of Table 3, and shown in Table 4, reveal that the coefficient for $T_{LOW}$ is 0.001. This means that if $T_{LOW}$ were 1 second and there was no time spent in any high pressure group (i.e. all 3 $T_{HIGH}$ values are zero), then $\Delta V$ would be only 0.001 Liter. Thus the leak rate at $P_{REFERENCE^-}$LOW is 0.001 L/sec. The same analysis can be repeated for each of the three $T_{HIGH}$ variables to produce the leak rate at the relevant $P_{REFERENCE}$. Since the $P_{REFERENCE}$ for each time variable is known (rightmost numbers in Table 4), the relation between pressure and leak rate can be established.

TABLE 3

| Interval # | $\Delta V$ | Norm $T_{LOW}$ | $T_{HIGH}$, GP1 | $T_{HIGH}$, GP2 | $T_{HIGH}$, GP3 |
|---|---|---|---|---|---|
| 1 | 0.20 | 1.05 | 0.63 | 0 | 0 |
| 2 | 0.10 | 1.03 | 0.35 | 0 | 0 |
| 3 | 0.32 | 1.11 | 0.94 | 0 | 0 |
| 4 | 0.46 | 1.12 | 0 | 1.07 | 0 |
| 5 | 0.90 | 1.16 | 0 | 0 | 1.61 |
| 6 | 0.50 | 0.62 | 0 | 0 | 1.00 |
| 7 | 0.18 | 2.65 | 0.60 | 0 | 0 |
| 8 | 0.16 | 1.29 | 0.43 | 0 | 0 |
| 9 | 0.36 | 1.50 | 0 | 0.80 | 0 |
| 10 | 0.59 | 1.37 | 0 | 1.38 | 0 |
| 11 | 0.80 | 1.04 | 0 | 0 | 1.54 |
| 12 | 0.52 | 0.93 | 0 | 1.35 | 0 |
| 13 | 0.23 | 1.11 | 0.78 | 0 | 0 |
| 14 | 0.42 | 1.06 | 0 | 0.96 | 0 |
| 15 | 0.41 | 5.14 | 0 | 0.97 | 0 |
| 16 | 0.50 | 1.22 | 0 | 1.17 | 0 |
| 17 | 1.44 | 1.19 | 0 | 0 | 2.57 |
| 18 | 0.80 | 0.89 | 0 | 0 | 1.61 |

TABLE 4

Regression Statistics

| r | 0.996 |
|---|---|
| r$^2$ | 0.992 |
| F | 1.400E−14 |
| Observations | 18 |

| Coefficients | $P_{REFERENCE}$ |
|---|---|
| Norm $T_{LOW}$ | 0.001 | 6.1 |
| $T_{HIGH}$, GP1 | 0.321 | 10.0 |
| $T_{HIGH}$, GP2 | 0.420 | 12.5 |
| $T_{HIGH}$, GP3 | 0.539 | 15.5 |

It is evident that if the dependent variable ($\Delta V$) and all the time variables were divided by the respective $T_{INTERVAL}$ for each INTERVAL, the results would be similar.

Figure 5:
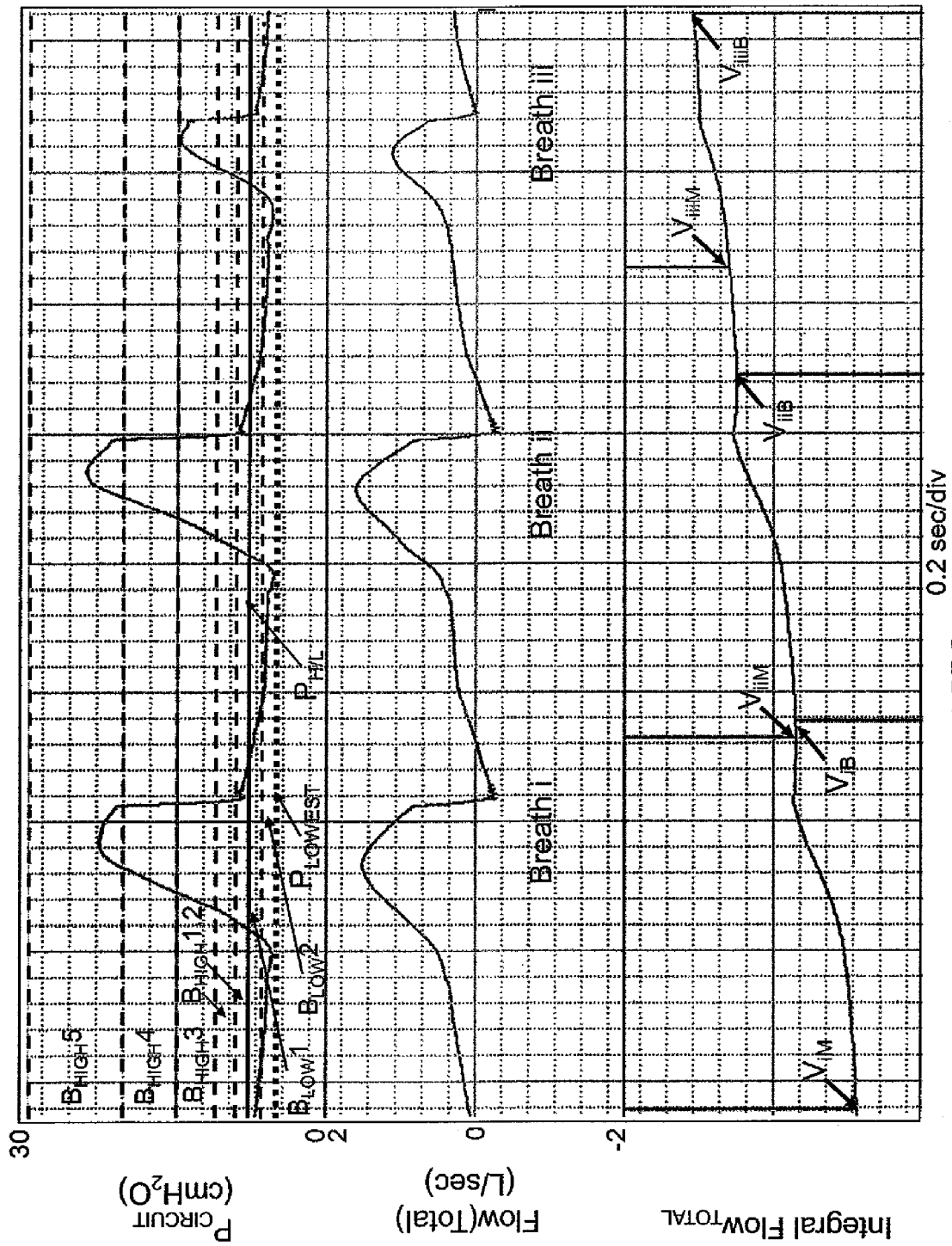
FIG. 5 contains graphical representations of a method of implementing the present invention.

C) Determining Time Spent in Selected Pressure Bins within Individual INTERVALs:

FIG. 5 illustrates this method of implementing the current invention. Here $\Delta V$ between selected expiratory points is calculated across a plurality of INTERVALs as has been described with other methods of implementation (bottom panel, FIG. 5). The duration of each INTERVAL is also measured ($T_{INTERVAL}$). The fraction of $T_{INTERVAL}$ spent within selected pressure ranges (bins) is then determined for each INTERVAL. FIG. 5, top, shows the pressure data from three breaths in the PAV mode. These breaths display some variability in peak pressure reached as well as in the duration of the high-pressure phase. The horizontal dashed lines are the boundaries of the pressure bins selected in this case. As can be seen, the height of the bins is not constant. The selection of bin heights (i.e. pressure range within the bin) may be based on the INTERVAL-to-INTERVAL variability in time spent in different pressure ranges. This selection is a compromise between the need to reduce, as much as possible, the pressure range within each bin, and the need to have enough INTERVAL-to-INTERVAL variability in time spent within each bin. The smaller the range of pressure within the bin, the lesser the impact of non-linearities in the pressure-flow rate relation of the leak on the results. Thus, with an infinitely small pressure range in the bin, the difference between the ratio [leak/pressure] at the lowest and the highest pressures within the bin is very small, regardless of the pressure-flow relation of the leak. On the other hand, if the pressure range in the bin is very small, it is less likely that much time will be spent in the bin and, by extension, less likely that there will be enough INTERVAL-by-INTERVAL variability in this time spent in the bin. I have found that the average time spent in a given bin (average of $T_{BIN}$ across INTERVALs) should preferably be >0.07 $T_{INTERVAL}$ and the average standard deviation of $T_{BIN}$ should preferably be >0.02. In one preferred embodiment bin selection proceeds as follows but it is recognized that other approaches can be used to achieve the desired compromise.

All the pressure data points within a given base-match interval (defined by the two selected expiratory points, iB-iM, FIG. 5 bottom) are sorted in order of increasing value. The lower pressure boundary of the lowest bin ($B_{LOW}$, FIG. 5 top) is defined by the lowest pressure value observed within the plurality of INTERVALs being processed ($P_{LOWEST}$, FIG. 5, top). In the example of FIG. 5, $P_{LOWEST}$ was 5.2 cmH$_2$O. Next, as was described in the first implementation, a pressure level is arbitrarily selected that roughly separates the high and low-pressure phases ($P_{H/L}$, solid line, FIG. 5 top). The number of pressure data points between $P_{LOWEST}$ and $P_{H/L}$ (lowest bin; $B_{LOW}$) is counted and divided by sampling rate, giving the time spent in the lowest pressure bin ($T_{LOW}$). Because $B_{LOW}$ contains most of the expiratory data points, the time spent in it (i.e. $T_{LOW}$) is invariably the longest of all other bins and has the greatest variability during assisted breathing. In one aspect of this invention, when the pressure range in $B_{LOW}$ is large, due to slow decline in pressure during expiration, $B_{LOW}$ is further divided into two or more pressure ranges ($B_{LOW}1$ and $B_{LOW}2$ ... etc). Next, pressure points above $P_{H/L}$ are separated into preliminary bins of a fixed pressure range. In one preferred embodiment, the preliminary bin height (i.e. pressure range) is 0.75 cmH$_2$O, but clearly other values can be selected. Thus, the first preliminary bin in the high-pressure range (preliminary $B_{HIGH}1$) extends from $P_{H/L}$ to $[P_{H/L}+0.75$ cmH$_2$O], and preliminary $B_{HIGH}2$ extends from $[P_{H/L}+0.75$ cmH$_2$O] to $[P_{H/L}+1.5$ cmH$_2$O], and so on until the highest pressure reached in all the INTERVALS under consideration is included. The time spent in each of these preliminary bins is calculated from the number of data points in the bin and sampling rate, thereby resulting in preliminary $T_{HIGH}1$, preliminary $T_{HIGH}2$, preliminary $T_{HIGH}3$, etc. Each preliminary $T_{HIGH}$ value is then divided by the corresponding $T_{INTERVAL}$ to result in preliminary $T_{HIGH}1/T_{INTERVAL}$, preliminary $T_{HIGH}2/T_{INTERVAL}$, etc. The appended Table (Table X below) is an example of data obtained in 25 consecutive INTERVALs, including the three shown in FIG. 5 (highlighted). The Table shows for each INTERVAL: $\Delta V/T_{INTERVAL}$, time spent in the lowest bin/$T_{INTERVAL}$ ($T_{LOW}$) as well as preliminary $T_{HIGH}1/T_{INTERVAL}$ to preliminary $T_{HIGH}14/T_{INTERVAL}$ with each of these preliminary high bins having a height of 0.75 cmH$_2$O. In this file there were 28 preliminary $T_{HIGH}$ bins because the peak pressure ranged up to 29 cmH$_2$O in some breaths. Values obtained in these higher bins are not shown to avoid clutter; the intent here is to describe the process of selecting bins. As can be seen, INTERVALs in which pressure does not include values in certain pressure ranges are assigned zero in the relevant preliminary $T_{HIGH}$ columns. For example, in breath 3 in FIG. 5 (breath #13 in the Table), pressure did not exceed 15 cmH$_2$O. Accordingly, it was assigned zero in all preliminary bins in which pressure is >15 (preliminary $T_H12$ and higher).

After a suitable number of INTERVALs have been obtained, the average and standard deviation (SD) of time spent in each bin is calculated. These values are shown at the bottom of Table X below for 25 INTERVALs. $T_{LOW}$ remains as a separate "final" bin in view of the large average and SD values. Although the average and SD of preliminary $T_{HIGH}1$ are above the desirable levels (0.07 and 0.02, respectively), the values of preliminary $T_{HIGH}1$ and preliminary $T_{HIGH}2$ are summed to form the first "final" high bin ($T_{HIGH}1$). It was decided arbitrarily to have a minimum pressure range in final bins of 1.5 cmH$_2$O to reduce computational time and since 1.5 cmH$_2$O is a small enough pressure range. The average time spent in preliminary $T_{HIGH}3$ is <0.07. So, the values in this column are combined with the values in the next two columns, such that the average of the combined values is now >0.07 (column Sum $T_H3$-$T_H5$). If the SD is >0.02, and it is in this case, the sum of preliminary $T_{HIGH}$ 3 to 5 becomes the second "final" high bin ($T_{HIGH}2$). If not, more preliminary columns are added until the average and SD both meet the minimum requirements. Starting from the next preliminary $T_{HIGH}$ column (preliminary $T_{HIGH}6$ in this case), the process is repeated until both the average and SD of the summed values exceed the minimum requirements. In this case the sum of $T_H6$-$T_H11$ met the criteria, and the sum of these columns became "final" $T_{HIGH}3$. This process continues until all preliminary bins are incorporated in "final" bins.

The average pressure within each final bin in each INTERVAL is calculated by summing all the pressure values within the bin and dividing by the number of data points. These individual average values are then averaged together for all the INTERVALs under consideration. The overall average serves as the reference pressure ($P_{REFERENCE}$) for that bin. An optional next step is to correct the time spent in each bin for differences between its average pressure and the overall average. For example, if average pressure in final bin 3 ($T_{HIGH}3$) in INTERVAL 5 is 10.6 cmH$_2$O but the overall (reference) pressure for bin 3 is 11.2, then final $T_{HIGH}3$ for INTERVAL 5 is corrected to the value that would result in the same pressure integral at reference pressure:

$$\text{Corrected } T_{HIGH}3 = T_{HIGH}3 * 10.6/11.2$$

Finally, the "final" $T_{HIGH}$ values are tabulated along with $T_{LOW}$ value(s), $\Delta V/T_{INTERVAL}$ and a number of other variables selected to minimize the contribution of $\Delta V_{PATIENT}$ to $\Delta V$ (section 1). An example of such Table is appended (Table Y below, derived from the same data as Table X). A multiple regression analysis is then performed with $\Delta V/T_{INTERVAL}$ as the dependent variable and all the other variables as independent variables. An example result, from the data of Table Y, is shown in Table 5 below. This Table shows that the correlation was excellent ($r^2=0.99$) and highly significant ($F=1.5\ E^{-10}$). From such regression results, it is possible to calculate the estimated leak rate in different bins by adding the intercept to the coefficient of the bin in question. Thus, for $T_{LOW}$, the leak is 0.627+(−0.202), or 0.424 L/sec and for $T_{HIGH}1$ it is 0.627+ (−0.114) or 0.513 L/sec, and so on. It is recognized that any of a number of mathematical methods can be used to extract the coefficients corresponding to the different bins from data such as those of Table Y. We have, however, found that multiple linear regression analysis provides adequate results.

TABLE 5

Regression Statistics

| | |
|---|---|
| r | 0.99 |
| $r^2$ | 0.99 |
| F | 1.50E−10 |
| Observations | 25 |

| | Coefficients |
|---|---|
| Intercept | 0.627 |
| $dT_{HIGH}$ | 0.028 |
| ddflow/dt | 0.183 |
| dmatch delta | −0.015 |
| dflow | −2.285 |
| $T_{INTERVAL}$ − $avgT_{INTERVAL}$ | 0.013 |
| $T_{LOW}$ | −0.202 |
| $T_{HIGH}1$ | −0.114 |
| $T_{HIGH}2$ | 0.009 |
| $T_{HIGH}3$ | 0.040 |
| $T_{HIGH}4$ | 0.117 |
| $T_{HIGH}5$ | 0.214 |

| $P_{REFERENCE}$ | Est. Leak | Actual Leak |
|---|---|---|
| 6.1 | 0.424 | 0.451 |
| 7.6 | 0.513 | 0.505 |
| 9.5 | 0.635 | 0.563 |
| 13.1 | 0.666 | 0.662 |
| 17.6 | 0.744 | 0.765 |
| 22.8 | 0.840 | 0.871 |

The bottom part of Table 5 shows the estimated leak for the different bins along with the reference pressure for each bin. From this data, it is possible to develop a mathematical function that describes the relation between circuit pressure and leak rate. In this case, the best-fit function was [Leak=$0.15P^{0.58}$]. This function, obtained from analysis of elapsed INTERVALs can then be used to estimate the instantaneous leak in real time.

The accuracy of this algorithm was tested as follows.

Figure 6:
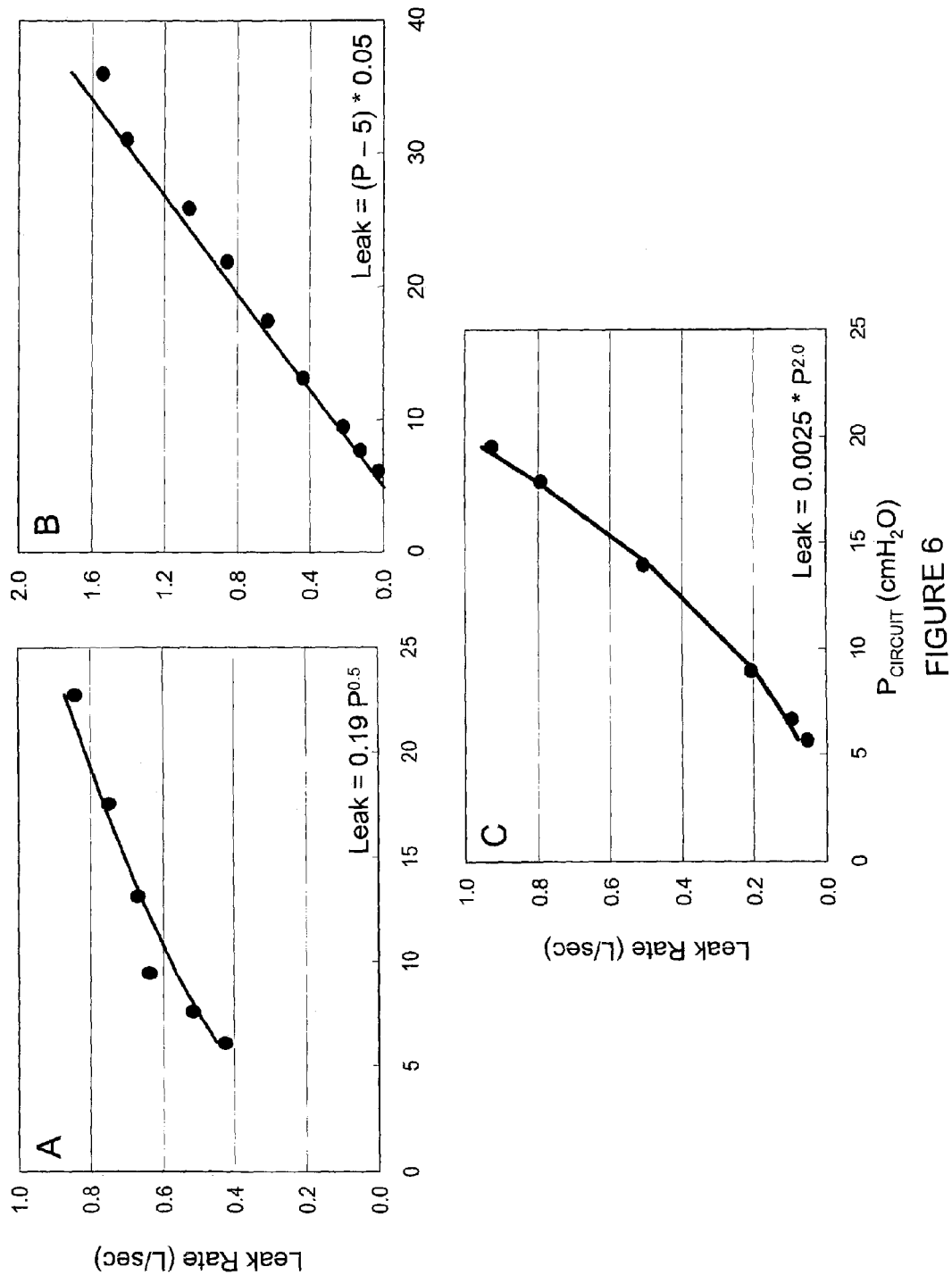
FIG. 6 contains graphical representations of the circuit pressure and flow measured in ventilator hose recorded from patients on invasive mechanical ventilation (PAV or pressure support (PSV))

A number of digital files containing circuit pressure and flow rate measured in the ventilator hose were used. These files were recorded from patients on invasive mechanical ventilation (PAV or pressure support (PSV)). Flow rate was free of leaks (average flow rate=0). To the flow rate signal we added a variable amount corresponding to a specified function of pressure. The corrupted flow rate was then processed by the software to see if it can accurately estimate the added amount (i.e. virtual leak) at different pressure points in the operating range. FIG. 6 shows three representative examples, two on PAV (6A and 6B) and one on PSV (6C). The solid line in each plot represents the actual (virtual) leak with the equation used inserted in the bottom right corner of each panel. The circles are the results obtained by the current algorithm of the invention. Panel A is from the file shown in Tables X and Y. The agreement between estimated and actual leak is obvious in all cases despite differences in the mode of ventilation and in the type of pressure-leak flow rate relation used.

D) Calculating the Integral of Pressure when Pressure is Processed According to Different Mathematical Functions:

Here, the pressure values enclosed between the selected base/match points are processed according to a number of mathematical functions. The following is a general function used in the preferred embodiment but clearly other functions (for example, exponential, polynomial . . . etc) can serve the purpose:

$$P_{PROCESSED} = (Pi - x)^Y$$

The same pressure points within each INTERVAL are processed using a range of X and Y values. The integral of the processed pressure values is obtained for each X,Y combination in each INTERVAL and this integral is divided by $T_{INTERVAL}$. As a result, a plurality of $T_{INTERVAL}$-normalized integral values is generated for each INTERVAL (INTEGRAL VALUES). Clearly, if the pressure profile is constant across INTERVALs, normalized $\Delta V$ (i.e. $\Delta V/T_{INTERVAL}$) will be constant and the INTEGRAL VALUES will also be constant across all INTERVALs, regardless of the X and Y values used. Under such conditions, it is not possible to identify the appropriate relation between pressure and leak flow rate. However, when pressure profile is variable between INTERVALs, normalized $\Delta V$ will vary and so will the INTEGRAL VALUES. It may be expected that the INTEGRAL VALUES generated using the function that is closest to the actual leak function will produce the best correlation with normalized $\Delta V$.

A number of standard statistical approaches can be used to obtain the best fit between the various INTEGRAL VALUES and normalized $\Delta V$. In the preferred embodiment, X values between −4 and plus 8, in increments of two, are used for a total of 7X values. For each X value, pressure is processed using 7 different Y values (0.3, 0.5, 0.7, 1.0, 1.5, 2.0 and 2.4). We found that these reasonably cover the various leak functions observed in practice. This treatment results in 49 different INTEGRAL VALUES for each INTERVAL. Clearly other X-Y ranges can be used. When a number of INTERVALS having suitable variability in pattern of pressure delivery has accumulated, regression analysis is performed between the normalized $\Delta V$, as the dependent variable, and the corresponding INTEGRAL VALUES using one of the 49 functions as the independent variable. The process is repeated using each of the 49 INTEGRAL VALUES. The other variables that aim to compensate for changes in $\Delta V_{PATIENT}$ are also included in each regression. As a result of this statistical treatment, 49 correlation coefficients are generated. The regression with the highest correlation is selected and the function used for pressure processing in this regression is then used to estimate the instantaneous leak in real time. For example, if the integral of $(P-4)^{1.5}$ gives the best correlation with normalized $\Delta V$, this function is assumed to accurately reflect the relation between pressure and leak flow rate.

Appended Table Z shows example data from application of this method in 25 consecutive INTERVALS. As with other approaches, $\Delta V$ across individual INTERVALS is the dependent variable. The different variables that minimize the contribution of $\Delta V_{PATIENT}$ to $\Delta V$ are listed in the next 5 columns. The next 13 columns contain the INTEGRAL VALUES when using 13 of the 49 different X,Y combinations. The other 36 columns are not included in this illustration to avoid clutter. From such data 49 regression calculations are produced, each with its own correlation coefficient. Table 6 below shows the ten regression functions with the best correlation ($r^2$). The one with the highest $r^2$ is highlighted. This function can be written as:

$$\Delta V/T_{INTERVAL} = 0.008 + 0.0006(P_{CIRCUIT}+2)^{2.4}$$

TABLE 6

| $r^2$ | X | Y | constant | coefficient |
|---|---|---|---|---|
| 0.981 | -2.00 | 2.40 | 0.008 | 0.0006 |
| 0.981 | -4.00 | 2.40 | -0.054 | 0.0005 |
| 0.980 | 2.00 | 2.00 | 0.046 | 0.0029 |
| 0.980 | 4.00 | 2.00 | 0.114 | 0.0034 |
| 0.980 | 0.00 | 2.40 | 0.068 | 0.0007 |
| 0.980 | 0.00 | 2.00 | -0.028 | 0.0026 |
| 0.980 | -2.00 | 2.00 | -0.105 | 0.0023 |
| 0.980 | 6.00 | 2.00 | 0.176 | 0.0040 |
| 0.979 | 2.00 | 2.40 | 0.124 | 0.0008 |
| 0.979 | 8.00 | 1.50 | 0.169 | 0.0202 |

Figure 7:
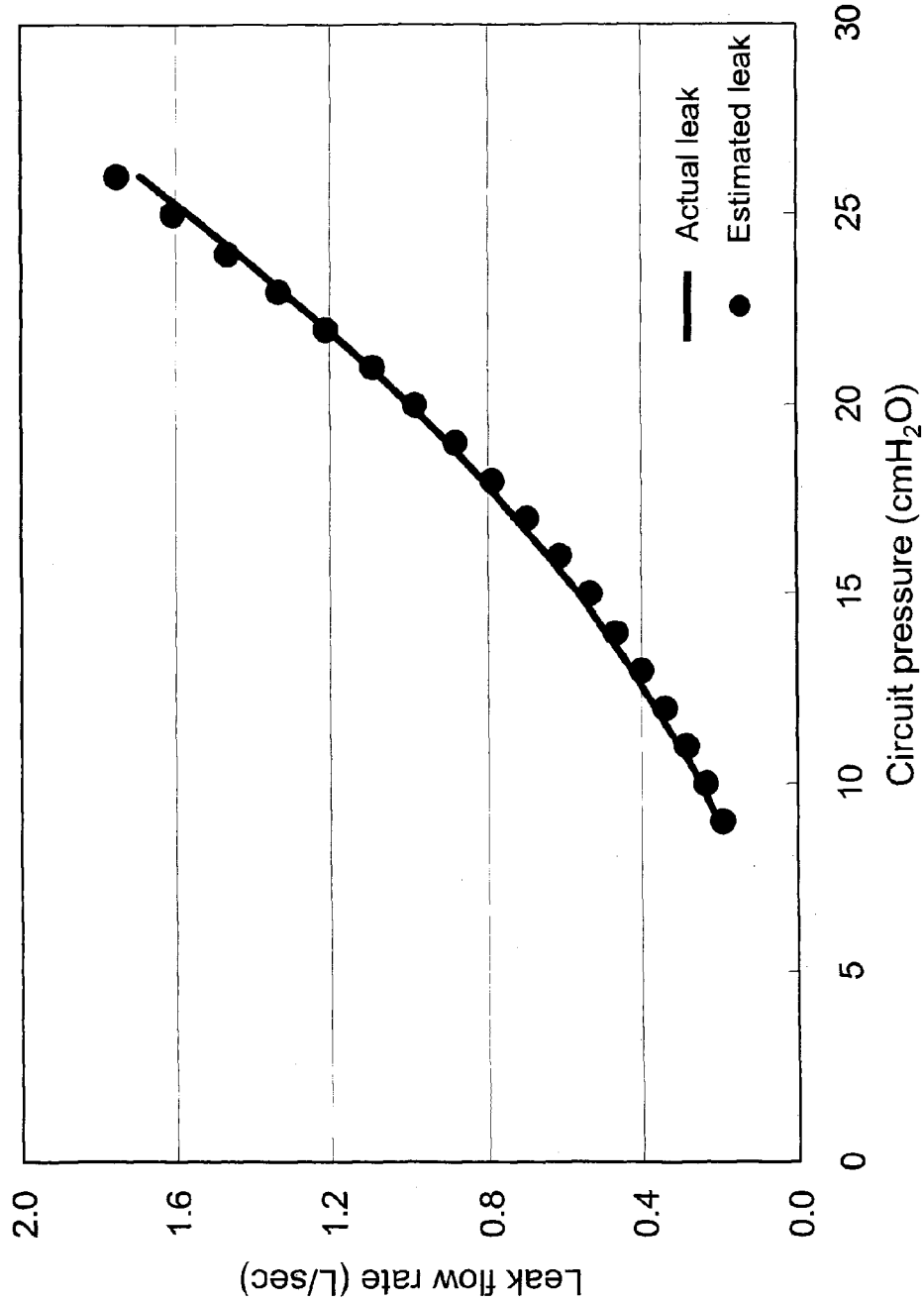
FIG. 7 contains a graphical representation of correlation of the function $\Delta V/T_{INTERVAL}=0.008+0.0006(P_{CIRCUIT}+2)^{2.4}$ with actual leak over a pressure range.

FIG. 7 shows that this function provides an excellent estimate of the relation between circuit pressure and actual leak rate over the pressure range that applied in this case (9 to 26 cmH$_2$O).

It is clear from Table 6 that $r^2$ was very high (>0.97) in all of the ten top regressions. Thus, any of these, and not necessarily the one with the highest $r^2$, can be used to estimate leak flow rate in the operating pressure range. For example, one may elect to use any function that is associated with an $r^2$ value greater than a specified amount.

Although the statistical approach described above to find the best-fit relation between $\Delta V$ and the various INTEGRAL VALUES provides satisfactory results, it is by no means the only approach. Any of a variety of non-proprietary methods, available in standard statistical methodology, can obviously be used to find the best-fit function from data, such as those in Table Z.

It is clear that satisfactory implementation of the current invention in any of its forms (for example, A to D above) requires the presence of sufficient variability in the pattern of pressure delivery among the various INTERVALS being used to estimate the relation between circuit pressure and leak rate. A number of indices can be used to assess the extent of said variability. In one embodiment, the ratio $T_{HIGH}/T_{INTERVAL}$ is used, where $T_{HIGH}$ is time spent in the high-pressure phase. Another suitable index is average pressure within the individual INTERVALs where said average is obtained from: [integral of pressure between base and match points/$T_{INTERVAL}$]. Yet another index is the ratio: $\Sigma(P_{HIGH} \cdot dt)/\Sigma(P_{INTERVAL} \cdot dt)$, where $\Sigma(P_{HIGH} \cdot dt)$ is the integral of pressure across the high-pressure phase and $\Sigma(P_{INTERVAL} \cdot dt)$ is the integral of pressure across $T_{INTERVAL}$. Clearly, many other indices can be used for this purpose.

Because success of the current invention depends on the presence of a suitable amount of variability in pattern of pressure delivery, it is advisable to monitor the extent of said variability in data sets being analyzed, and to implement steps that insure the presence of sufficient variability. Accordingly, in another aspect of this invention, an index of variability is monitored. For example, the microprocessor can track the coefficient of variation of a suitable index of pressure pattern variability (see immediately preceding paragraph) in a suitable number of preceding INTERVALs (for example, 10). When the coefficient falls below a threshold amount (for example, 0.07) a signal is issued to the pressure control circuitry to alter one or more aspects of pressure delivery in some selected breaths such that the coefficient of variation rises above the desirable level. The aspect to be deliberately altered would necessarily vary depending on the ventilation mode used. For example, in PSV the ventilator may vary the pressure level or cycling off threshold in some breaths, whereas in PAV it may increase or decrease the % assist in selected breaths or delay or advance cycling off.

PREFERRED EMBODIMENT

Two embodiments were built. The first was a non-real time system used to develop, test and refine the algorithms. This embodiment utilized a desktop computer and the algorithms were coded using the Matlab system. It incorporated all the four methods proposed to generate indices that reflect pattern of pressure delivery (Methods 2A to 2D in the Detailed Description of the Invention section). Testing of this embodiment was done using digital files recorded previously, which contained signals corresponding to circuit pressure and flow rate measured during mechanical ventilation of several patients. The original flow rate signals in these files did not incorporate any leaks as they were obtained during invasive ventilation with a tight tracheal seal. A virtual leak was added to the flow rate signal by generating a new channel (Flow+Leak) comprised of the original flow rate signal plus a function related to the recorded circuit pressure, representing a specified leak function. A variety of leak functions were added to the true flow rate signal to test the accuracy of the different algorithms (2A to 2D) in estimating leak under various possible sources of leak (see, for example, FIG. 6). The circuit pressure and (Flow+Leak) data are downloaded into computer memory and are sampled at 200 Hz (This high sampling frequency was used because it was the sampling frequency of the original files; such high sampling frequencies are not essential).

The testing performed using the non-real time system allowed us to determine optimal values and tools to be used within the algorithms (for example, optimal pressure ranges within bins in method 2C, amount of variability in pressure pattern needed to obtain reliable results, preferred statistical methods . . . etc). This testing also established that all four proposed methods of pressure processing yielded adequate results (see section 2). In particular, it established that Method 2A can provide acceptable results with only two data sets, corresponding to two Base-Match INTERVALs (or breaths). It further established that of the four methods proposed for analysis of multiple breaths (Methods 2A to 2D), method 2A is the preferred approach when few Base-Match Intervals are available (for example, at start-up or soon after a change in leak characteristics) while in the presence of data from many INTERVALs (for example, ≥10), method 2D was the simplest to apply and was more accurate.

The current invention is intended for use inside commercial ventilators. Virtually all commercial ventilators in current use are computer-based. It is envisioned that the algorithms of the present invention will be implemented using code written for the specific computers within the commercial ventilators. Furthermore, since measurement of flow rate and circuit pressure are standard in all commercial ventilators, the flow rate and circuit pressure signals required for implementation of the current invention can be obtained directly from the ventilator. Because it was not practicable to introduce new code in an existing commercial ventilator, we constructed a standalone real time computer system to serve as a preferred embodiment. In view of our experience with the non-real time system, we implemented method 2A for estimating the leak when few INTERVALs are available and method 2D for leak estimation when ≥10 INTERVALs are available. This embodiment also calculates all the Delta values needed to minimize the contribution of true changes in lung volume ($\Delta V_{PATIENT}$) to $\Delta V$ (section 1 of Detailed Description of the Invention), and incorporates algorithms to detect changes in leak characteristics and to send messages when leak characteristics have changed or when variability in pattern of pressure delivery is less than optimal so that steps can be taken by the ventilator to increase variability.

Figure 8:
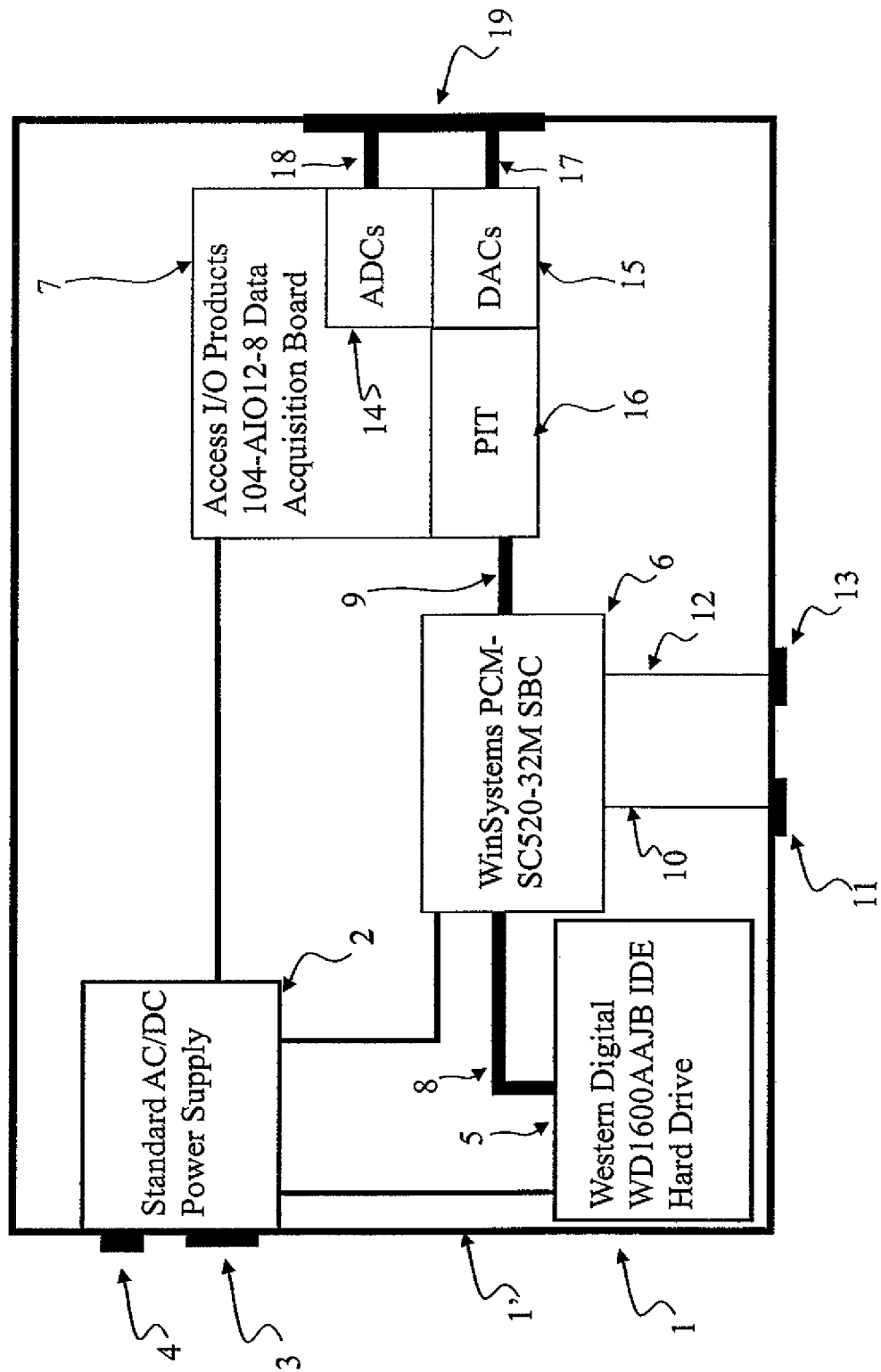
FIG. 8 is a schematic view of a prototype of a standalone device for carrying out an embodiment of the present invention.

I. Description of the Hardware:

FIG. 8 is a diagram of the Standalone prototype (1) with its various components. It consists of a metal enclosure (1') (WinSystems ENC-104-13) which houses a standard AC to DC power supply (2) that converts the 120 Volt 60 Hz. AC signal to ±12 Volts DC and ±5 Volts DC for use by the internal hardware components (5,6,7) The power supply (2) is controlled by means of a switch (4) accessible on the outside of the enclosure (1). The AC input into the power supply (2) is connected via a standard male three prong connector (3), which connects to a standard power supply cable plugged into a standard 120 Volt AC wall outlet.

The hard drive (5) is interfaced to the Single Board Computer (6) via a standard IDE connection cable (8). The Single Board Computer (6) is interfaced to the Access I/O Products 104-AIO12-8 Data Acquisition Board (7) via an edge connector and cable (9) specified by the PC104 specification. The Single Board Computer (6) has external digital input and output capabilities defined by the EIA 232 standard. A custom internal cable (10) connects the Single Board Computer (6) to a standard DB9 connector (11) mounted on the metal enclosure (1). The Single Board Computer (6) also has external communications capabilities defined by the IEEE 802.x Ethernet standard. A custom internal cable (12) connects the Single Board Computer (6) to a standard RJ45 connector (13) mounted on the metal enclosure (1).

The data acquisition board (7) has capabilities of 8 channels of 12 bit analog to digital conversion (ADC) (14) as well as four channels of 12 bit digital to analog conversion (DAC) (15). The data acquisition board also has real time interrupt capabilities via a Periodic Interrupt Timer (PIT) (16). The ADCs are connected via a custom internal cable (18) to a standard terminal block (19) mounted on the outside of the enclosure (1). The DACs are connected via a custom internal cable (17) to a standard terminal block (19) mounted on the outside of the enclosure (1). Analog signal input and output is then achieved by connecting signals or volt meters/acquisition systems to the standard terminal block (19).

The data acquisition board (7) has capabilities of 8 channels of 12 bit analog to digital conversion (ADC) (14) as well as four channels of 12 bit digital to analog conversion (DAC) (15). The data acquisition board also has real time interrupt capabilities via a Periodic Interrupt Timer (PIT) (16). The ADCs are connected via a custom internal cable (18) to a standard terminal block (19) mounted on the outside of the enclosure (1). The DACs are connected via a custom internal cable (17) to a standard terminal block (19) mounted on the outside of the enclosure (1). Analog signal input and output is then achieved by connecting signals or volt meters/acquisition systems to the terminal block pins (19).

It is, of course, evident that many similar configurations of various size, scale, processing power, and accuracy could be used to demonstrate and implement the embodiment described herein. This is of descriptive nature for a particular device only and should not be construed as restricting the possible implementations of the concepts contained herein.

Execution Description

The power supply (2) is connected to a suitable AC power source via (3), and suitable pressure and flow rate signals are connected to the standard terminal block (19). The flow rate signal inputted here is the raw signal incorporating the leak, referred to here as FlowLeak. It is typically derived from a dedicated flow meter within the ventilator or external ventilator circuit but can also be any signal that varies with flow rate in a predictable manner, regardless of how it is obtained. In non-invasive ventilation systems, leaks usually have two components, intentional and unintentional. The intentional leak is built into the circuit to facilitate $CO_2$ removal. The unintentional leak results when there are loose connections between the interface and the patient or between different components of the circuit or if there are open holes in the circuit. Since the ventilator manufacturer usually knows the pressure-flow characteristics of the intentional leak, the manufacturer may elect to subtract the intentional leak from the total flow rate before inputting it into the embodiment of the current invention. In this case, the embodiment of the current invention would estimate only the unintentional leak.

It is advantageous but not required to connect a data acquisition device, oscilloscope or similar device to the terminal block connecter (19) also to monitor the real time Leak and true flow rate signals. It is necessary to connect another computer or terminal to the Single Board computer (6) via the DB9 connector (11) utilizing a standard RS232 interface protocol.

The power switch (4) is turned on and the single board computer (6) will start and load the operating system (LINUX) from the Hard Drive (5) into its resident memory. The operating system will then automatically load and execute the Leak Detection software which is resident on the Hard Drive (5). The Leak detection software will then output some information via the serial port (11) about the program.

Figure 9:
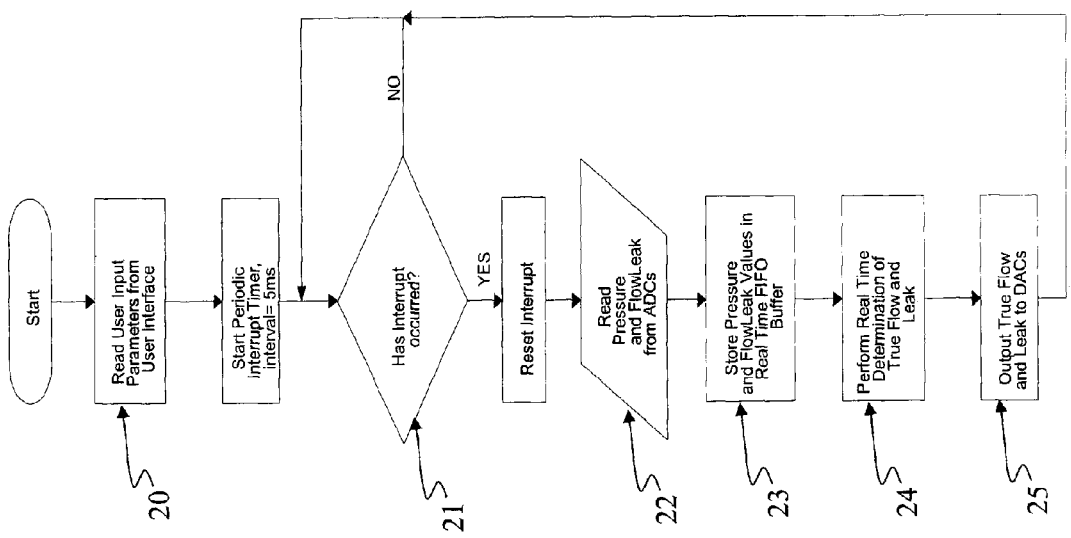
FIG. 9 is a flow sheet of real time process for carrying out an embodiment of the present invention.
Figure 10:
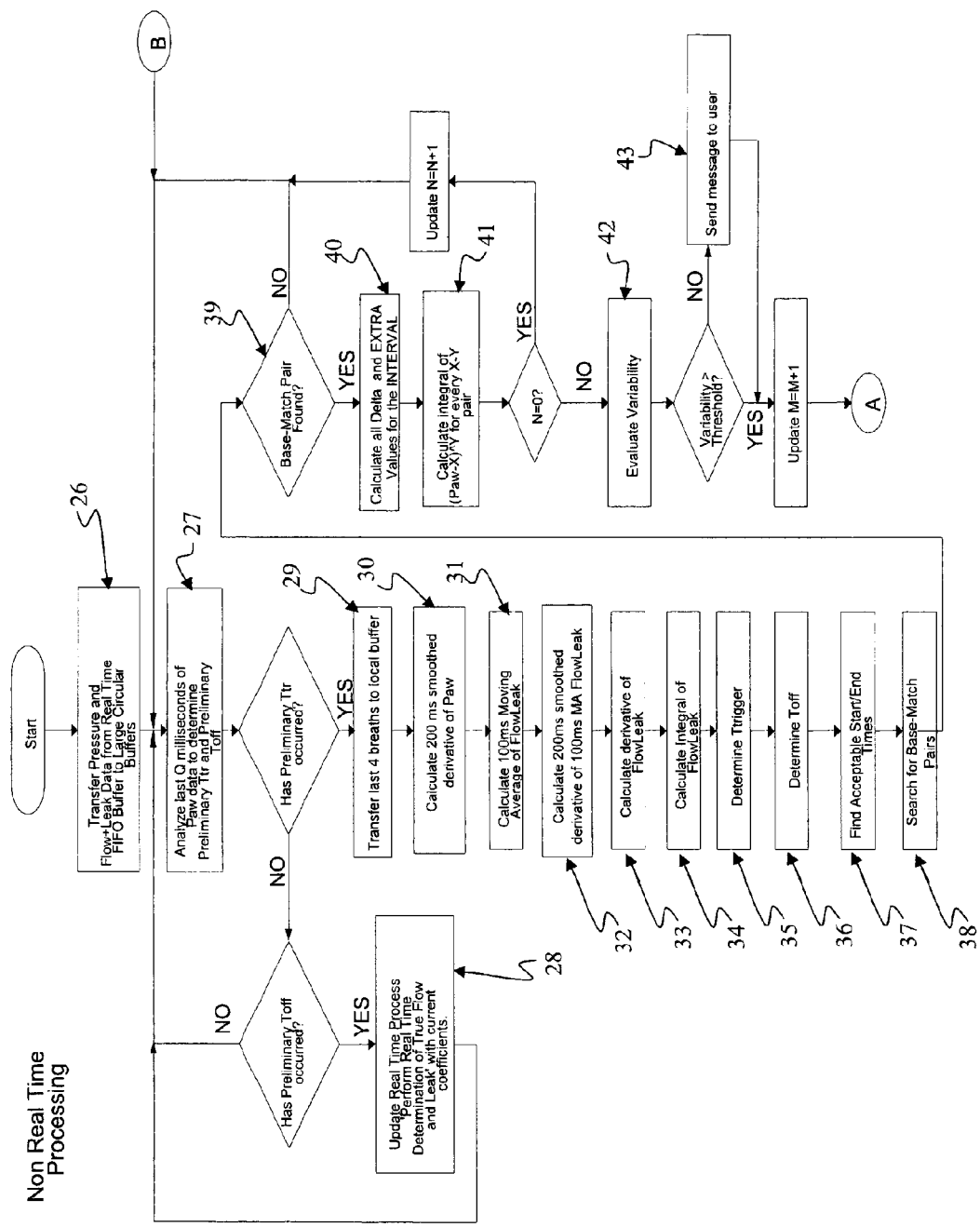
FIGS. 10 and 11 are flow sheets of a non-real time processing estimation program for carrying out an embodiment of the present invention.
Figure 11:
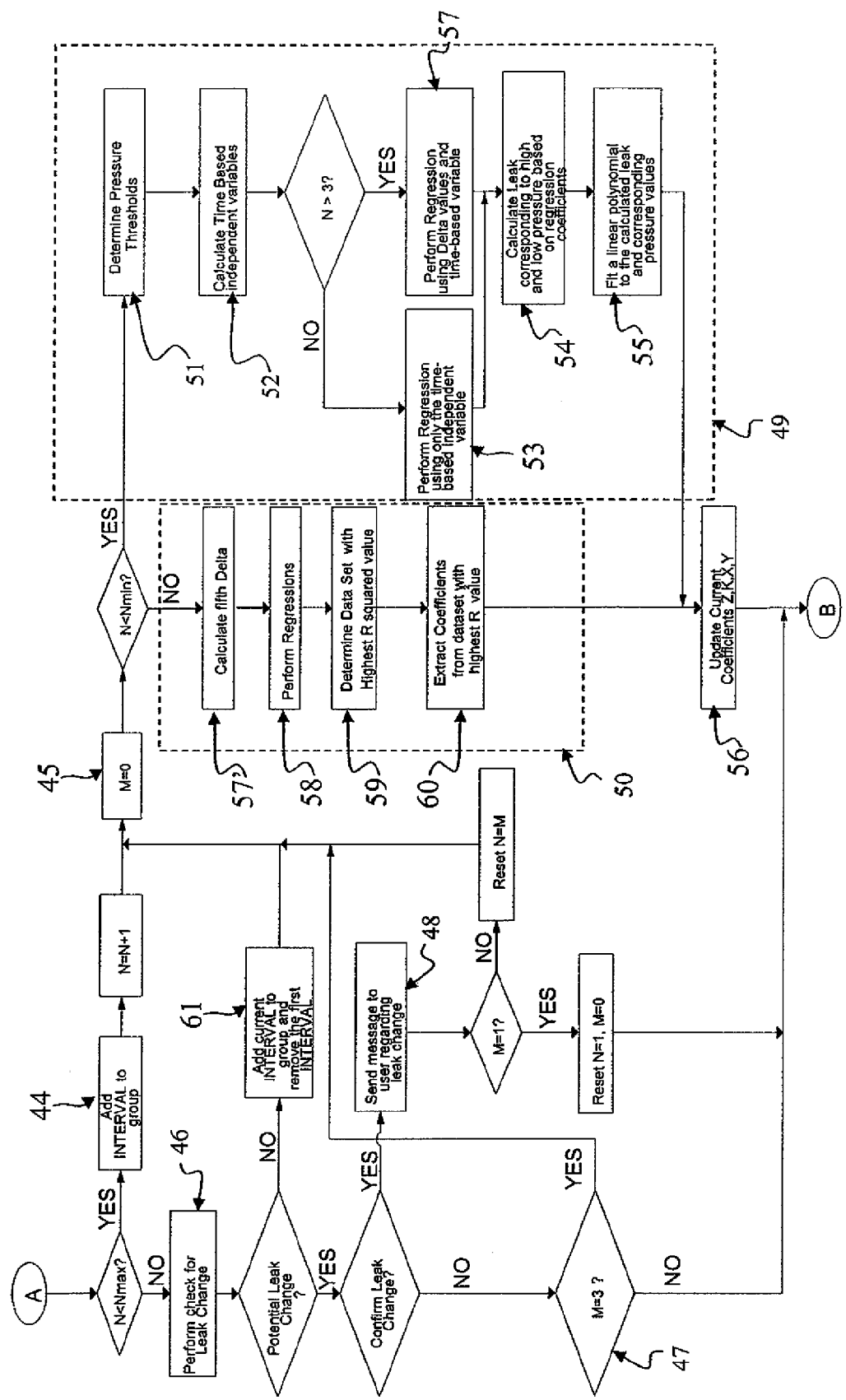

The user needs to type the proper commands into the terminal software as well as set the initial user parameters before the program begins executing in real time. After execution, the system follows the logical program flow as specified in the flowcharts (FIGS. 9 to 11).

II. User Inputs:

The user inputs listed below were included in the preferred embodiment for A) development purposes, to help fine-tune the optimal thresholds, constants, desired number of indices . . . etc, in light of experience, and B) to be used in determining the onset (Ttrigger) and end (Toff) of the high pressure phase of the respiratory cycle. These inputs would not be necessary when the current invention is embedded in commercial ventilators since default values can be used for the inputs listed under A, and the Ttrigger and Toff signals can be imported directly from the ventilator's control system.

A) Inputs Used for Development Purposes: The following is a list of current user inputs in this category. The system is, however, designed so that new user inputs can be introduced that can alter any of the reference values used in many of the system's software processes.

a) $N_{MIN}$: Number of Base-Match INTERVALs available since start-up, or since a change in leak, below which the simplified method (Method 2A) is used and at or above which the more complex method (Method 2D) is used. (Default is 10).

b) Minimum CV: The value of coefficient of variation below which a message is sent out requesting a change in pattern of pressure delivery to increase variability (see section IV B 8, below). (Default is 0.07).

c) Minimum $T_{HIGH}/T_{INTERVAL}$ difference: The difference in $T_{HIGH}/T_{INTERVAL}$ between two successive INTERVALs at start up and following a change in leak below which a message is sent out requesting a change in pattern of pressure delivery to increase variability (see section IV B 8, below). (Default is 0.10).

d) Thresholds for identifying a change in leak characteristics (see section section IV B 12):
   Threshold A: The low residual threshold (default A=0.045);
   Threshold B: Number of Standard Deviations required (default B=3.5);
   Threshold C: The high residual threshold (default C=0.185);
   Threshold D: The threshold for the average of two residuals from two successive INTERVALs (default D=0.095);
   Threshold E: The threshold for the average of three residuals from three successive INTERVALs (default E=0.065).
e) XY ranges: The range of X and Y values to be used in generating the various indices that describe pressure pattern in method 2D (see section IV B 7) (default X values are −4, −2, 0, 2, 4, 6 and 8 and default Y values are 0.3, 0.5, 0.7, 1.0, 1.5, 2.0 and 2.4 for a total of 49 combinations).
f) Default Z, K, X and Y: The values of Z, K, X and Y to be used at start up (default values are 0, 0, 0, and 0) (see section IV B 11).
g) $N_{MAX}$: Maximum number of INTERVALs to be used in the regression (default=20).

B) Inputs to be used to identify preliminary Ttrigger and Toff (see section IV B 1):
   a) Ttrigger Threshold: Pressure threshold used to identify preliminary Ttrigger in quasi-real time (see section IV B 1). This is generally set at 3-5 $cmH_2O$ above the Positive END Expiratory Pressure (PEEP).
   b) Toff Threshold: Pressure threshold used to identify preliminary Toff in quasi-real time (see section IV B 1). This is generally set at 1-2 $cmH_2O$ below Ttrigger Threshold.
   c) Ttrigger Scan frequency (Q): Frequency at which the computer checks for a Ttrigger (default is every 500 msec).

III. Real Time Processes:

FIG. 9 is a flow chart of the Real Time processes. The first step is to read user inputs from the user interface (20). The Periodic Interrupt Timer (PIT) (16, FIG. 8) sends an interrupt every 5 ms (this can be set to different times, as needed). When an interrupt occurs (21), the Pressure and FlowLeak are read from the ADCs (14 in FIG. 8) (22). The Pressure and FlowLeak data are stored a Real-Time FIFO buffer (23) from which they will be transmitted to the Non-Real-Time Parametric Estimation Program (FIG. 10). The current Pressure and FlowLeak data are then processed (24) to calculate the current leak value and the current estimated patient flow rate (i.e. current FlowLeak−current leak value).
Current leak is estimated from:

$$\text{Current Leak} = Z + K(P-X)^Y$$

P is circuit pressure and Z, K, X and Y are constants obtained from the regression procedure implemented in the Non-Real-Time Parametric Estimation Program (FIG. 11) and are updated every time a regression calculation is performed on the stored data, which is typically after every breath. The current leak value and the current estimated patient flow rate are then outputted (24) to the DACs (15, FIG. 8) from which they may be monitored or used externally by ventilator equipment as desired.

IV. Non-Real Time Processes

The non-real time processes are illustrated in FIGS. 10 and 11.

A) OVERVIEW: Non-real time analysis is done on data collected over a period encompassing four previous preliminary Ttriggers and is updated with every new preliminary Ttrigger. With every new preliminary Ttrigger, a search is made to identify a definitive Ttrigger and the preceding cycling-off point (Toff). Next, a search is made for two points (Base-Match points) with matching FlowLeak and derivative of FlowLeak. The Base point is invariably in the expiratory phase immediately preceding the new Ttrigger while the matching point could be in any of the last three expiratory phases (usually a match is found in the immediately preceding expiratory phase). Once a Base-Match pair is identified, a number of calculations are made using the data in the interval between the Base and Match points (INTERVAL). The difference in integrated FlowLeak between the two points is measured ($\Delta V$), and this forms the dependent variable. Five independent variables that reflect the contribution of true changes in lung volume to $\Delta V$, collectively called Deltas, are measured (section 1D in Detailed Description of the Invention section). Then, all the pressure data within the INTERVAL are processed according to the following equation:

$$P_{PROCESSED} = (P-X)^Y$$

The processed pressure is integrated between the Base and Match points resulting in one value for the particular X and Y values used. The process is repeated for each X-Y combination. The number of X and Y values to be used is a user input (see section IIA). Typically we use seven X values and seven Y values, resulting in 49 different integrated pressure values for each INTERVAL. The length of INTERVAL is calculated ($T_{INTERVAL}$). This is used to normalize all dependent and independent variables. Finally, five EXTRA values are collected for use to implement the simplified leak estimation method (Method 2A) in the event there are few INTERVALs available for analysis. The 61 values collected from each INTERVAL ($\Delta V$, $T_{INTERVAL}$, the five Deltas, the 49 pressure integrals and the five EXTRA values) are transferred into the regression table, forming a row available for the regression analysis.

As new INTERVALs are processed, the regression table accumulates more data. When the number of available rows is 2 to 9, regression is performed using the simplified method and employing normalized $\Delta V$ as the dependent variable and a value derived from the five EXTRA values as the main independent variable. The Delta values are incorporated in the regression in a step fashion as the number of rows increases. This analysis produces a description of the leak characteristics of the form: Leak=Z+K*P (see section 2A). This equation has the same form as the general leak equation (Leak=Z+K(P−X)$^Y$) with both X and Y being zeroes.

When the number of available rows equals or exceeds $N_{MIN}$ (default=10), the more complex method of leak estimation is used, with normalized $\Delta V$ as the dependent variable and the five Deltas and one of the 49 integrated pressure values serving as the independent variables. The process is repeated with each X-Y combination used to process the pressure data. This results in X*Y regressions of the form [Leak=Z +K(P−X)$^Y$], each with its own level of significance ($r^2$). The regression with the highest $r^2$ is chosen and the values of Z, K, X and Y in this regression are transferred to the real time processing module for use in generating the estimated leak and estimated true patient flow rate in real time.

The software also incorporates an algorithm for detecting a change in leak characteristics (i.e. relation between instantaneous pressure and instantaneous leak) as may occur with loosening of the mask straps with head movement or other actions. Every new $\Delta V$ is compared with the $\Delta V$ expected from the existing regression when applied to the specific independent variables associated with that new $\Delta V$ (Delta values, integrated pressure . . . etc). When the deviation from expected $\Delta V$ exceeds a specified threshold, a change in leak is declared and a search for new coefficients begins starting with the first breath that deviated from expected behavior. The old regression coefficients continue to be used until the new coefficients are found, usually within two to three breaths.

The preferred embodiment also incorporates an algorithm that monitors variability in the pattern of pressure delivery, as expressed by the coefficient of variation (CV) of the ratio of $T_{HIGH}/T_{INTERVAL}$ or the difference in this ratio between two breaths. When this ratio (or difference, when there are two breaths) is below a threshold value (currently a user input, II A b and II A c), a message is sent out to the user interface. When embedded in a ventilator, this message would trigger a change in pattern pressure delivery. The specific way of changing the pattern would be determined by the ventilator manufacturer based on the method of control of pressure in use at the time.

B) SPECIFIC FUNCTIONS: The data stored in the FIFO buffer (23) are continuously transferred to large circular buffers (26) that hold up to six minutes of pressure and FlowLeak data. The following steps then follow:

1. Determination of Preliminary Ttrigger and Toff (27): This step is unnecessary in embedded systems since Ttrigger and Toff can be imported from the ventilator's control system. However, in this freestanding system it was necessary to implement such a step. All non-real time processes are performed on blocks of data that end with a Ttrigger. Thus, identifying when a Ttrigger occurred is necessary to determine the data block to be examined. Identifying when a Toff occurred is done to determine the time at which the latest regression coefficients for leak estimation should be transferred to the Real Time module (28) for calculation of current estimated leak (24). It is advantageous to update the real time coefficients at a point when circuit pressure is low so that when there is a significant change in leak characteristics between updates the step change in estimated leak would be minimized. At this stage (27) only preliminary determinations of Ttrigger and Toff are made. More definitive determinations of Ttrigger and Toff are done later (35, 36).

Identification of Preliminary Ttrigger and Toff (27) is performed by scanning the data stored in the large circular buffers (26) in the last 1.0 second. This process is repeated every Q second so that the intervals analyzed overlap. Q is a user input (section II B c, default 500 ms). A preliminary Ttrigger is identified when Pressure increases from below a Trigger Threshold (user input II B a) to above that threshold and remains above it for >200 ms. In the freestanding embodiment this Threshold is typically selected to be 3 to 5 cmH$_2$O above PEEP. A preliminary Toff is identified when Pressure decreases from above a Toff Threshold (user input II B b) to below that threshold and remains below it for >200 ms. In the freestanding embodiment this is typically selected to be 1 to 2 cmH$_2$O below Trigger Threshold to insure that when a Toff is identified (200 ms after pressure crosses threshold) circuit pressure is very close to PEEP.

When a preliminary Ttrigger is identified, a block of data (Pressure and FlowLeak) is transferred from the large circular buffer to smaller local Pressure and FlowLeak buffers (29). In the current embodiment, the data stored since [current Ttrigger−three Ttriggers] or in the last 60 seconds, whichever is shorter, is transferred to the local buffer. This is because analysis of every new breath may require information from as far back as three past breaths (see Search for Base-Match pairs (38)).

2. Preliminary Calculations (30 to 34): The data in the local buffers (29) are processed to produce a number of variables needed for subsequent steps: These are:
 a. 200 ms smoothed derivative of Pressure (30). The current derivative value reflects the rate of change in pressure over the past 200 ms (i.e. it is not centered). This is dPaw.
 b. 100 ms moving average (MA) of FlowLeak (31). This is MA FlowLeak.
 c. 200 ms centered smoothed derivative of MA of FlowLeak (32). This is dMA FlowLeak.
 d. Derivative of FlowLeak (33). This is dFlowLeak.
 e. Integral of FlowLeak (34).

3. Determine definitive Ttrigger (35): This step is unnecessary in embedded systems as the real Ttrigger can be imported from the ventilator's control system. In the freestanding embodiment of the current invention Ttriggers are identified by scanning the pressure data in the local buffer for points that meet either of the two following criteria:
 a. dPaw (30) increases from below 5 to above 5 and remains above 5 for 100 ms AND Pressure increases by 2 cmH$_2$O AND continuously increases within 500 ms, or
 b. dPaw (30) increases from below 3 to above 3 and remains above 3 for 300 ms.

4. Determine Definitive Toff (36): dPaw (paragraph 2a above) is scanned in the interval between preceding Ttrigger and the latest Ttrigger looking for negative values that are below a Threshold (Negative Transients). The interval begins at the preceding Ttrigger and ends at one of the following two points:
 a. If the distance between the latest Ttrigger and preceding Ttrigger is greater than the mean of the distances between all successive Ttriggers, the end point is found by adding 1 second and the minimum of the distances between all successive Ttriggers to the time of the preceding Ttrigger.
 b. If the above distance condition is not met, then the interval ends at two-thirds of the distance between the preceding and latest Ttriggers.

The threshold is [0.8*minimum dPaw in the interval] unless [0.8*minimum dPaw] is less than −50 cmH$_2$O/s in which case threshold is −30 cmH2O. A 200 ms search window for Toff is formed based on the distribution of the data points below threshold:
 a. If all values below threshold are contiguous (i.e. there is only one Negative Transient), the search window is the 200 ms preceding the minimum value within this negative transient.
 b. If there are two or more Negative Transients with ≥1 s separating the first two transients, the search window is the 200 ms preceding the minimum value within the first negative transient.
 c. If there are two Negative Transients separated by a gap <1s, the search window is the 200 ms preceding the minimum value within the negative transient containing the lower dPaw.
 d. If there are >2 negative transients with <1 s separating the first two transients, the search window is the 200 ms preceding the minimum value within the first two negative transients.

The differences between successive dPaw values within the 200 ms window are calculated. The minimum of the differences is identified. Toff is that point −50 ms.

5. Find Base-Match Points (37,38): The objective of this algorithm is to find a point in one of the previous three expiratory phases that has MA FlowLeak (31) and dMA FlowLeak (32) values similar to a point within the latest expiratory phase. The two points must fall within acceptable search regions inside the respective expiratory phases. The first step is to define the acceptable regions within each expiratory phase (37). An expiratory phase is the interval between a Toff and the next Ttrigger. The start of an acceptable search region is 200 ms after the point of maximum expiratory flow rate (minimum MA FlowLeak (31)) within the expiratory phase. Next, a temporary interval is defined that starts at the more recent of the start of the acceptable search region and Ttrigger–600 ms. A preliminary end of the search region is defined as the earlier of [Ttrigger–200 ms] or the point with the highest dMA FlowLeak (32) from the start of the interval to [(Ttrigger–200 ms]. This preliminary end point is overruled if one of the following conditions is met:

a. A search of dMA FlowLeak (32) within the temporary interval finds a period ≥50 ms of consecutive negative values that includes any value <–0.3 L/s/s. In this case the entire search region is invalidated and no data is collected from this expiratory phase.

b. A search of dMA FlowLeak (32) indicates that there are not any positive values. In this case the entire search region is invalidated and no data is collected from this expiratory phase.

c. There is one or more points where dMA FlowLeak increases from below to beyond the minimum positive value plus 5% of the difference between the maximum and minimum positive dMA FlowLeak (32) and the most recent of such points occurs earlier than Ttrigger–200 ms, in which case that most recent point would be used instead of Ttrigger–200 ms.

If none of the above conditions are met, the end of the acceptable search region is set to Ttrigger–200 ms.

The second step is to identify Base-Match points within acceptable search regions (38). The search is done first in the nearest expiratory phase with an acceptable search region (usually the preceding breath). Points within the current and previous acceptable search regions that have similar MA FlowLeak (31) (within ±0.01 L/s) and dMA FlowLeak (32) (within ±0.1 L/s/s) are identified. This is achieved as follows:

a. Initial Base and Match search regions are limited according flow: the higher of the MA FlowLeak (31) minima becomes the lower limit, and the lower of the MA FlowLeak (31) maxima becomes the upper limit.

b. The start and end times of those time intervals are applied to the dMA FlowLeak (32) also.

c. For each value of MA FlowLeak (31) and corresponding dMA FlowLeak (32) of the limited Base interval, find the time point(s) of the limited Match interval where the MA FlowLeak (31) of the Base interval is within ±0.01 L/s of the MA FlowLeak (31) values of the Match interval, AND the dMA FlowLeak (32) of the Base interval is within ±0.1 L/s/s of the dMA FlowLeak (32) of the Match interval. For every match so found, the difference between the Base and Match MA FlowLeak (31) and one-tenth the difference between the Base and Match dMA FlowLeak (32) are calculated, and the absolute values of those differences are summed, and the resulting values are multiplied by the absolute value of the Base MA FlowLeak (31). This is called Product. If there are more than one matches in the Match interval, the time point corresponding to the minimum Product is considered a valid match for the corresponding Base interval value (if there are matching minima, the one that is most recent is used). After iterating through all values of MA FlowLeak (31) and corresponding dMA FlowLeak (32) of the Base interval, the minimum of those minimum Products identifies the Match time point and the iteration of the Base interval corresponding to that minimum Product identifies the Base time point.

If no matching point is found in the preceding expiratory phase, or the preceding phase is invalid (per 5a, above), the search is performed in the expiratory phase two breaths before. This process continues until a match is found or the data in the local buffers (29) are exhausted (three previous breaths or 60 seconds).

If no matching point is found for the latest expiratory phase, no further analysis is done on this breath (39). If a new Base-Match pair is found the process continues (39).

6. Calculate Delta and Extra Values (40): The following values are calculated for each Base-Match INTERVAL and entered as a row in the regression table. Ttrigger identifies the time of the INTERVAL:

a. $T_{INTERVAL}$: Duration of INTERVAL (Base point–Match point).

b. $\Delta V/T_{INTERVAL}$: The difference in Integral of FlowLeak (paragraph 2e, above) between Base and Match points divided by current $T_{INTERVAL}$. This is the dependent variable in the regression.

c. High Integral ($\Sigma(P_{HIGH} \cdot dt)$): Integral of unprocessed pressure between the preliminary Toff and the preceding preliminary Ttrigger within INTERVAL.

d. Low Integral ($\Sigma(P_{LOW} \cdot dt)$): Integral of unprocessed pressure between the preliminary Toff and next preliminary Ttrigger.

e. $P_{HIGH}$: The pressure value at the definitive Toff.

f. $P_{LOW}$: The pressure value at the Base point.

g. $T_{HIGH}/T_{INTERVAL}$: Total time spent in the high pressure zone within INTERVAL divided by $T_{INTERVAL}$.

h. $dT_{HIGH}/T_{INTERVAL}$: Current $T_{HIGH}/T_{INTERVAL}$ minus previous $T_{HIGH}/T_{INTERVAL}$ divided by current $T_{INTERVAL}$.

i. $dFlowLeak/T_{INTERVAL}$: [FlowLeak at Base point minus FlowLeak at Match point] divided by current $T_{INTERVAL}$.

j. $ddFlowLeak/T_{INTERVAL}$: [dFlowLeak at Base point (33) minus dFlowLeak at Match point (33)] divided by current $T_{INTERVAL}$.

k. $dmatch\ delta/T_{INTERVAL}$: The quotient of [(Base point minus preceding Toff) minus (Match point minus Toff preceding it)] divided by the mean of [(Base point minus preceding Toff) and (Match point minus Toff preceding it)], divided by current $T_{INTERVAL}$.

The final delta value, current $T_{INTERVAL}$–average $T_{INTERVAL}$, is calculated for all entries in the regression table just before performing the regression since it requires knowledge of all $T_{INTERVAL}$s to be used in the regression function.

7. Calculate Integral of $(Paw-X)^Y$ for each X-Y pair (41): To obtain the modified pressure values, for every INTERVAL, calculate $(Paw-X)^Y$ for every combination of X and Y. The ranges of X and Y values to be used are defined in the user input (section II A e, above; 49 pairs by default). Then, for each X and Y combination, calculate the integral of the resulting pressure values over the INTERVAL. Divide the integral by $T_{INTERVAL}$. This produces X*Y independent variable for each INTERVAL. Save these values per INTERVAL in a matrix (there are 49 columns, and one row per INTERVAL).

8. Check the Extent of Variability (42): This is done when the number of rows in the regression table (N) is >1. If N=2, variability is the difference in $T_{HIGH}/T_{INTERVAL}$ between the two INTERVALS. If the difference is <a user input (section II A c, default is 0.1), a message is sent to the user interface (43) suggesting that pressure pattern should be made more variable to improve the leak estimates. In embedded systems this message would not necessarily be displayed but would preferably automatically trigger a change in cycling off threshold of the ventilator so that $T_{HIGH}$ varies between breaths according to an algorithm designed by the ventilator manufacturer. If N is >2, the coefficient of variation of $T_{HIGH}/T_{INTERVAL}$ for all INTERVALs (maximum 20) is calculated and if <the value inputted by the user (section II A b, default is 0.07), the same message (43) is sent out.

9. Subsequent Processing (FIG. 11): With addition of data from a new INTERVAL to the table N is incremented by 1. Subsequent processing depends on the value of N, as described in FIG. 11. If N is less than a maximum value ($N_{MAX}$, User Input, section II A g, default=20), data from new INTERVALs are added without any deletion of earlier data (44). A different counter (counter M (45)) is reset to 0. If N≥$N_{MAX}$, a check is first made to determine if there has been a change in leak characteristics (46). If there is no suspected change in leak then the new data is added to the table and the first set is deleted. Counter M (45) is also reset to zero. This leaves data from $N_{MAX}$ INTERVALs. If there is a suspected change in leak characteristics, M is not reset to zero and no deletions from the table occur until the leak change has been either confirmed or rejected. However, the INTERVAL(s) within suspected leak change will not be used in a regression until a leak change has been either confirmed or rejected. The process of confirmation takes 1 to 3 new INTERVALs (see section 12, below). During this time, M is incremented by 1 with each new INTERVAL before a leak change is confirmed, and no new regression analysis is performed (the regression coefficients obtained before the suspected leak change continue to be fed to the real time process). If the Perform check for Leak Change function (46) could not confirm a leak after three INTERVALs (47), depending on the conditions met within that function (see section IV B 12, below), either the first two rows in the table are deleted, and the most recent two rows are kept in the table (and the earliest of the last three rows is removed from the table), returning N to $N_{MAX}$, M is reset to 0, and a new regression calculation is made, OR the most recent three rows are removed from the table and regression coefficients remain unchanged while awaiting new INTERVALs. If a change in leak is confirmed, a message is sent to the user interface indicating that a change in leak characteristics has occurred (48). If the change in leak is confirmed by only one INTERVAL, N is reset to equal M and M is reset to zero, no new regression is performed while awaiting new INTERVALs, and the old regression coefficients are not updated. If the change in leak was confirmed based on two or three INTERVALs, N is reset to equal M and M is reset to zero. The simplified regression (49) is then performed on the data until N increases to specified minimum value ($N_{MIN}$, User Input, section II A a, default=10), at which time the more complex regression (50) is performed.

10. The Simplified Regression (49): This method is performed when N is >1 and <$N_{MIN}$ (default=2 to 9 INTERVALs). The process follows the steps outlined in Method 2A of the Detailed Description of the Invention:

a. Calculate a reference low pressure ($P_{LOW}$REF) from the average of all $P_{LOW}$ values available in the regression table (51). $P_{LOW}$ is one of the EXTRA values calculated from each INTERVAL and tabulated (section IV B 6f).

b. Calculate a reference high pressure ($P_{HIGH}$REF) from the average of all $P_{HIGH}$ values available in the regression table (51). $P_{HIGH}$ is one of the EXTRA values calculated from each INTERVAL and tabulated (section IV B 6e).

c. For each INTERVAL, calculate a modified $T_{HIGH}$ from $(\Sigma(P_{HIGH}\cdot dt))/(P_{HIGH}REF)$ (52). $\Sigma(P_{HIGH}\cdot dt)$ is one of the EXTRA values calculated from each INTERVAL and tabulated (section IV B 6c).

d. For each INTERVAL, calculate a modified $T_{LOW}$ from $(\Sigma(P_{LOW}\cdot dt))/(P_{LOW}REF)$ (52). $\Sigma(P_{LOW}\cdot dt)$ is one of the EXTRA values calculated from each INTERVAL and tabulated (section IV B 6d).

d. For each INTERVAL, calculate a modified $T_{INTERVAL}$ from modified $T_{HIGH}$ plus modified $T_{LOW}$ (52).

f. For each INTERVAL, calculate a modified $T_{HIGH}$/modified $T_{INTERVAL}$ (52).

g. For each INTERVAL, calculate a modified $\Delta V/T_{INTERVAL}$ from tabulated $\Delta V/T_{INTERVAL}$*Modified $T_{INTERVAL}/T_{INTERVAL}$.

h. If ≤3 INTERVALS are available in the table, perform linear regression analysis between modified $\Delta V/T_{INTERVAL}$ (dependent variable) and modified $T_{HIGH}$/modified $T_{INTERVAL}$ (dependent variable) (53, see Method 2A of the Detailed Description of the Invention). Then perform the following steps (54, 55, 56):

Obtain the leak rate at $P_{LOW}$REF (54) from:

Leak rate at $P_{LOW}$REF=Intercept of the regression.

Obtain the leak rate at $P_{HIGH}$REF (54) from:

Leak rate at $P_{HIGH}$REF=sum of the slope and intercept of the regression.

Obtain the relation between leak rate and pressure (55, as in FIG. 4) by fitting a linear polynomial to the calculated leak rates and corresponding pressures, generating the equation: Leak rate=Z+K*P, where K is calculated from:

$K$=(Leak at $P_{HIGH}$REF−Leak at $P_{LOW}$REF)/($P_{HIGH}$REF−$P_{LOW}$REF),

And the intercept, Z, is calculated from:

$Z$=Leak at $P_{LOW}$REF−$P_{LOW}$REF*$K$

Update current coefficients Z, K, X, Y (56): In this simplified regression the values of Z and K obtained from step 55 are transferred to the buffer containing the regression coefficients while X and Y are each set to 0.

i. If N is >3 but <$N_{MIN}$ intervals, perform multiple linear regression analysis using $\Delta V/T_{INTERVAL}$ as the dependent variable and modified $T_{HIGH}$/modified $T_{INTERVAL}$ and one or more Delta values as the independent variables (57). The Delta values are added to the regression as N increases in the following order: $dT_{HIGH}/T_{INTERVAL}$, ddFlowLeak/$T_{INTERVAL}$, dmatch delta/$T_{INTERVAL}$, dFlowLeak/$T_{INTERVAL}$ (section IV B 6). By INTERVAL 7 all four Deltas are included in the regression. The fifth delta ($T_{INTERVAL}$−average $T_{INTERVAL}$) is not included in this regression. The regression calculation results in an intercept (Z) and coefficients for each of the independent variables used. As in the previous step (i), the intercept is used as estimated leak rate at $P_{LOW}$REF and the sum of the intercept and the coefficient of modified $T_{HIGH}$/modified $T_{INTERVAL}$ is the estimated leak rate at $P_{HIGH}$REF. Subsequent steps are similar to those of the previous step (55, 56).

11. Regression Analysis when N is between $N_{MIN}$ and $N_{MAX}$ (50): First a new Delta variable, $T_{INTERVAL}$−average $T_{INTERVAL}$, is calculated for each INTERVAL in the table (57'). The average of all $T_{INTERVAL}$S is calculated and is subtracted from each individual $T_{INTERVAL}$ to produce the fifth Delta.

This step is followed by multiple linear regression analysis (58) with $\Delta V/T_{INTERVAL}$ as the dependent variable and the independent variables consisting of the five Deltas and one of the pressure integrals. As indicated earlier (41), a number of Integral pressure values is generated from each INTERVAL with the number being X*Y (User Inputs, section IV A e, default=49). In this step, one Integral is used at a time in the regression. Each calculation results in an intercept (Z) and coefficients for each of the five Deltas as well as a coefficient for the pressure Integral used, which is unique to an X-Y combination. Each regression calculation also generates an index of the goodness of fit (r-squared) and a confidence interval represented by the standard deviation (SD) around the regression line.

After each regression, a check is performed on the residuals of the regression. If there are residuals that are outside of 2.5 SD of the residuals, rows of the regression table corresponding to those residuals are excluded, and the regression is performed on the remaining rows, generating new results.

When regressions for all the XY combinations used have been performed the regression with the highest r-squared that has a constant coefficient that is between −0.05 and 0.4 is selected (59). The regression coefficients in the buffer (56) are then updated with the values of Z (intercept of the best regression), K (coefficient of the pressure Integral in the best regression) and X and Y being the X and Y values in the best regression (60).

12. Check for Leak Change Process (46): The process begins when the data of a new INTERVAL are entered in the table and N is $\geq N_{MAX}$. The coefficients in the buffer (56) are used to estimate a $\Delta V$ for the new entry, given the Delta values and the pressure Integral (using the same X and Y values of the best regression) of the new INTERVAL. This estimate is compared to the $\Delta V$ entered for this new INTERVAL. The difference is divided by the SD of the regression obtained from the best regression, thereby producing the number of SDs by which the new $\Delta V$ deviates from the prediction based on the previous leak estimation coefficients. These two values, difference between predicted and actual $\Delta V$ (Residual) and number of SDs are used to determine whether a change in leak characteristics has occurred according to the following algorithm.

A leak change can be defined based on one, two, or three successive INTERVALs that meet the following conditions:

a. A leak change is rejected if Residual is <threshold A OR if number of SDs is <threshold B. Thresholds A and B are user inputs (section IV A d, defaults values are 0.045 and 3.5, respectively). In such case, the new INTERVAL is accepted in the table and the first entry in the table is deleted (61).

b. A leak change is confirmed after one INTERVAL (M=1) if Residual exceeds threshold C and number of SDs is >threshold B. Threshold C is a user input (section IV A d, default=0.185). In such case, only the new INTERVAL is added to the table all other entries are removed and N is reset to one. A new regression is not performed pending the entry of another INTERVAL. The real time process continues to use the old regression coefficients in the interim. When a second INTERVAL is entered (N=2) a simplified regression is performed and the resulting coefficients are used to update the buffer containing the coefficients (56).

c. If Residual is >threshold A but <threshold C and number of SDs is >threshold B, a potential leak change exists. Confirmation or rejection requires additional INTERVALs. A leak change is confirmed after the next INTERVAL is entered (M=2) if the absolute values of Residual and number of SDs for the second INTERVAL exceed thresholds A and B respectively, AND the Residual values of the first and second INTERVALs are of the same sign, AND either the absolute value of Residual for the second INTERVAL exceeds threshold C or the absolute value of the average of the Residuals of the first and second INTERVALs exceeds threshold D. Threshold D is a user input (section IV A d, default=0.095). If a leak change is confirmed at this point, N is set to 2 and a simplified regression is performed on the last two entries. The resulting coefficients are used to update the buffer containing the coefficients (56).

d. If the above conditions are not met, but the absolute value of Residual of the second INTERVAL exceeds threshold C, a leak change is confirmed based on the second INTERVAL by itself. Keep only the second INTERVAL, and reset M=1.

e. If neither of the above two conditions is met, a new regression is not performed pending the entry of a third INTERVAL. The real time process continues to use the old regression coefficients in the interim. When a third INTERVAL is entered in the table, a leak change is confirmed if:

i. The absolute values of Residual and #SD of the second INTERVAL exceed thresholds A and B respectively, AND the absolute value of the average of the last three Residuals exceeds threshold E (section IV A d, default=0.065), AND the Residuals of the first two INTERVALs have the same sign, OR ii. The absolute values of Residual and #SD of the second INTERVAL exceed thresholds A and B respectively, AND the absolute value of the average of the last three Residuals exceeds threshold E, AND third INTERVAL Residual >threshold A AND the Residuals of the second and third INTERVALs have the same sign AND number of SDs of third INTERVAL >B, OR iii. The absolute values of Residual and #SD of the second and third INTERVALs exceed thresholds A and B respectively, AND the Residuals of the second and third INTERVALs have the same sign, AND average of the second and third residuals >threshold D.

a. If leak change is confirmed by criteria i, a new simplified regression is performed using the last three INTERVALs. If leak change is confirmed by criteria ii or iii, a new simplified regression is performed using the last two INTERVALs only and M is reset to 2. A message is sent to the user interface to signal a change in leak characteristics. If leak change is not confirmed by any of the above criteria, M is reset to zero and the Regression process resumes using the 20 INTERVALs that occurred prior to the last three INTERVALs, unless the absolute value of the average of the last three residuals did not exceed threshold E and Residual and #SD in the second and third INTERVALs did not exceed thresholds A and B respectively in which case the first two INTERVAL entries in the table would be removed and last two INTERVAL entries would be kept in the table, and the earliest of the last three INTERVALs would be removed from the table.

SUMMARY OF THE DISCLOSURE

In summary of this disclosure, the present invention provides for estimating gas leakage from a ventilator circuit in which there is breath-by-breath or time-to-time variability in the pattern of pressure delivery by the ventilator. Modifications are possible within the scope of the invention.

TABLE X**

| INTERVAL # | dV | $T_{LOW}$ | prel.$T_H$1 | prel.$T_H$2 | Sum $T_H$1-$T_H$2 | prel.$T_H$3 | prel.$T_H$4 | prel.$T_H$5 | Sum $T_H$3-$T_H$5 | prel.$T_H$6 |
|---|---|---|---|---|---|---|---|---|---|---|
| 1 | 0.44 | 0.768 | 0.032 | 0.026 | 0.058 | 0.029 | 0.032 | 0.113 | 0.174 | 0.000 |
| 2 | 0.56 | 0.446 | 0.099 | 0.057 | 0.156 | 0.023 | 0.015 | 0.013 | 0.051 | 0.008 |
| 3 | 0.44 | 0.760 | 0.043 | 0.027 | 0.070 | 0.023 | 0.030 | 0.117 | 0.170 | 0.050 |

TABLE X**-continued

| | | | | | | | | | |
|---|---|---|---|---|---|---|---|---|---|
| 4 | 0.53 | 0.518 | 0.111 | 0.051 | 0.162 | 0.021 | 0.018 | 0.020 | 0.059 | 0.014 |
| 5 | 0.53 | 0.508 | 0.117 | 0.059 | 0.176 | 0.020 | 0.015 | 0.015 | 0.049 | 0.011 |
| 6 | 0.52 | 0.555 | 0.122 | 0.024 | 0.146 | 0.020 | 0.018 | 0.015 | 0.053 | 0.022 |
| 7 | 0.52 | 0.556 | 0.111 | 0.032 | 0.143 | 0.020 | 0.022 | 0.022 | 0.063 | 0.020 |
| 8 | 0.51 | 0.572 | 0.111 | 0.035 | 0.146 | 0.021 | 0.019 | 0.017 | 0.058 | 0.015 |
| 9 | 0.53 | 0.513 | 0.089 | 0.022 | 0.111 | 0.022 | 0.018 | 0.014 | 0.053 | 0.021 |
| 10 | 0.55 | 0.454 | 0.110 | 0.092 | 0.203 | 0.018 | 0.014 | 0.016 | 0.049 | 0.013 |
| 11 | 0.54 | 0.457 | 0.099 | 0.099 | 0.197 | 0.035 | 0.017 | 0.012 | 0.064 | 0.010 |
| 12 | 0.55 | 0.460 | 0.099 | 0.083 | 0.183 | 0.043 | 0.014 | 0.012 | 0.069 | 0.012 |
| 13 | 0.49 | 0.641 | 0.083 | 0.023 | 0.107 | 0.016 | 0.018 | 0.018 | 0.052 | 0.016 |
| 14 | 0.49 | 0.680 | 0.071 | 0.015 | 0.085 | 0.012 | 0.011 | 0.010 | 0.034 | 0.009 |
| 15 | 0.43 | 0.795 | 0.065 | 0.057 | 0.122 | 0.084 | 0.000 | 0.000 | 0.084 | 0.000 |
| 16 | 0.58 | 0.482 | 0.075 | 0.063 | 0.138 | 0.047 | 0.013 | 0.013 | 0.072 | 0.023 |
| 17 | 0.66 | 0.318 | 0.066 | 0.062 | 0.128 | 0.059 | 0.050 | 0.019 | 0.128 | 0.020 |
| 18 | 0.61 | 0.311 | 0.104 | 0.110 | 0.213 | 0.076 | 0.014 | 0.010 | 0.100 | 0.010 |
| 19 | 0.54 | 0.589 | 0.056 | 0.058 | 0.114 | 0.041 | 0.026 | 0.009 | 0.076 | 0.004 |
| 20 | 0.56 | 0.511 | 0.079 | 0.054 | 0.133 | 0.048 | 0.040 | 0.013 | 0.101 | 0.020 |
| 21 | 0.61 | 0.400 | 0.063 | 0.054 | 0.117 | 0.041 | 0.025 | 0.007 | 0.073 | 0.007 |
| 22 | 0.58 | 0.427 | 0.078 | 0.065 | 0.142 | 0.012 | 0.009 | 0.009 | 0.030 | 0.008 |
| 23 | 0.53 | 0.541 | 0.111 | 0.034 | 0.145 | 0.016 | 0.012 | 0.010 | 0.038 | 0.010 |
| 24 | 0.57 | 0.462 | 0.073 | 0.055 | 0.128 | 0.051 | 0.012 | 0.010 | 0.073 | 0.023 |
| 25 | 0.47 | 0.712 | 0.054 | 0.020 | 0.073 | 0.017 | 0.015 | 0.020 | 0.051 | 0.030 |
| Mean | 0.534 | 0.537 | 0.085 | 0.051 | 0.136 | 0.033 | 0.019 | 0.021 | 0.073 | 0.011 |
| SD | 0.055 | 0.130 | 0.025 | 0.026 | 0.040 | 0.020 | 0.010 | 0.029 | 0.037 | 0.006 |

| INTERVAL # | prel.$T_H7$ | prel.$T_H8$ | prel.$T_H9$ | prel.$T_H10$ | prel.$T_H11$ | Sum $T_H6$-$T_H11$ | prel.$T_H12$ | prel.$T_H13$ | prel.$T_H14$ |
|---|---|---|---|---|---|---|---|---|---|
| 1 | 0.000 | 0.000 | 0.000 | 0.000 | 0.000 | 0.000 | 0.000 | 0.000 | 0.000 |
| 2 | 0.011 | 0.011 | 0.013 | 0.011 | 0.009 | 0.065 | 0.011 | 0.011 | 0.051 |
| 3 | 0.000 | 0.000 | 0.000 | 0.000 | 0.000 | 0.050 | 0.000 | 0.000 | 0.000 |
| 4 | 0.010 | 0.012 | 0.020 | 0.016 | 0.014 | 0.084 | 0.010 | 0.012 | 0.014 |
| 5 | 0.015 | 0.015 | 0.013 | 0.011 | 0.011 | 0.075 | 0.011 | 0.013 | 0.013 |
| 6 | 0.020 | 0.015 | 0.015 | 0.015 | 0.015 | 0.104 | 0.049 | 0.060 | 0.033 |
| 7 | 0.012 | 0.018 | 0.016 | 0.014 | 0.012 | 0.091 | 0.010 | 0.014 | 0.052 |
| 8 | 0.012 | 0.015 | 0.012 | 0.010 | 0.012 | 0.075 | 0.015 | 0.025 | 0.048 |
| 9 | 0.014 | 0.020 | 0.014 | 0.010 | 0.012 | 0.090 | 0.067 | 0.105 | 0.067 |
| 10 | 0.014 | 0.011 | 0.013 | 0.009 | 0.013 | 0.072 | 0.013 | 0.011 | 0.009 |
| 11 | 0.008 | 0.010 | 0.008 | 0.010 | 0.008 | 0.055 | 0.008 | 0.008 | 0.010 |
| 12 | 0.014 | 0.012 | 0.009 | 0.012 | 0.009 | 0.069 | 0.009 | 0.009 | 0.007 |
| 13 | 0.016 | 0.021 | 0.021 | 0.057 | 0.070 | 0.201 | 0.000 | 0.000 | 0.000 |
| 14 | 0.010 | 0.009 | 0.010 | 0.020 | 0.039 | 0.098 | 0.008 | 0.028 | 0.024 |
| 15 | 0.000 | 0.000 | 0.000 | 0.000 | 0.000 | 0.000 | 0.000 | 0.000 | 0.000 |
| 16 | 0.011 | 0.009 | 0.015 | 0.012 | 0.011 | 0.080 | 0.007 | 0.007 | 0.011 |
| 17 | 0.008 | 0.008 | 0.008 | 0.006 | 0.007 | 0.057 | 0.006 | 0.007 | 0.006 |
| 18 | 0.012 | 0.010 | 0.008 | 0.010 | 0.008 | 0.058 | 0.010 | 0.010 | 0.012 |
| 19 | 0.005 | 0.004 | 0.005 | 0.006 | 0.005 | 0.029 | 0.005 | 0.005 | 0.004 |
| 20 | 0.007 | 0.007 | 0.006 | 0.006 | 0.006 | 0.051 | 0.006 | 0.005 | 0.006 |
| 21 | 0.008 | 0.007 | 0.006 | 0.006 | 0.007 | 0.040 | 0.006 | 0.008 | 0.008 |
| 22 | 0.009 | 0.008 | 0.008 | 0.008 | 0.009 | 0.050 | 0.011 | 0.012 | 0.125 |
| 23 | 0.007 | 0.010 | 0.012 | 0.009 | 0.012 | 0.060 | 0.007 | 0.009 | 0.010 |
| 24 | 0.006 | 0.007 | 0.010 | 0.007 | 0.006 | 0.059 | 0.007 | 0.005 | 0.008 |
| 25 | 0.027 | 0.049 | 0.068 | 0.000 | 0.000 | 0.174 | 0.000 | 0.000 | 0.000 |
| Mean | 0.010 | 0.014 | 0.012 | 0.011 | 0.012 | 0.071 | 0.011 | 0.015 | 0.021 |
| SD | 0.006 | 0.010 | 0.013 | 0.011 | 0.014 | 0.043 | 0.015 | 0.023 | 0.029 |

TABLE Y**

| INTERVAL # | dV | $dT_{HIGH}$ | ddflow/dt | dmatch delta | dflow | $T_{INTERVAL}$-avg$T_{INTERVAL}$ | $T_{LOW}$ | $T_{HIGH}1$ | $T_{HIGH}2$ | $T_{HIGH}3$ | $T_{HIGH}4$ | $T_{HIGH}5$ |
|---|---|---|---|---|---|---|---|---|---|---|---|---|
| 1 | 0.443 | −0.403 | −0.001 | −0.396 | 0.003 | −0.935 | 0.768 | 0.058 | 0.174 | 0.000 | 0.000 | 0.000 |
| 2 | 0.563 | 0.296 | −0.002 | 0.175 | −0.002 | −0.137 | 0.446 | 0.156 | 0.051 | 0.065 | 0.283 | 0.000 |
| 3 | 0.440 | −0.497 | 0.002 | −0.252 | −0.001 | −1.000 | 0.760 | 0.070 | 0.170 | 0.050 | 0.000 | 0.000 |
| 4 | 0.535 | 0.201 | 0.000 | 0.195 | −0.002 | −0.170 | 0.518 | 0.162 | 0.059 | 0.084 | 0.178 | 0.000 |
| 5 | 0.527 | 0.015 | 0.001 | 0.043 | 0.002 | −0.095 | 0.508 | 0.176 | 0.049 | 0.075 | 0.192 | 0.000 |
| 6 | 0.518 | −0.071 | 0.003 | −0.126 | −0.001 | −0.326 | 0.555 | 0.146 | 0.053 | 0.104 | 0.142 | 0.000 |
| 7 | 0.517 | 0.032 | 0.000 | 0.020 | −0.001 | −0.189 | 0.556 | 0.143 | 0.063 | 0.091 | 0.147 | 0.000 |
| 8 | 0.513 | 0.000 | 0.000 | −0.009 | 0.001 | −0.150 | 0.572 | 0.146 | 0.058 | 0.075 | 0.150 | 0.000 |
| 9 | 0.534 | 0.073 | 0.000 | −0.037 | 0.002 | −0.186 | 0.513 | 0.111 | 0.053 | 0.090 | 0.244 | 0.000 |
| 10 | 0.553 | −0.002 | 0.000 | 0.134 | −0.003 | −0.083 | 0.454 | 0.203 | 0.049 | 0.072 | 0.089 | 0.134 |
| 11 | 0.536 | 0.000 | 0.000 | 0.066 | 0.003 | −0.002 | 0.457 | 0.197 | 0.064 | 0.055 | 0.067 | 0.161 |
| 12 | 0.553 | −0.028 | 0.033 | −0.015 | 0.004 | −0.064 | 0.460 | 0.183 | 0.069 | 0.069 | 0.060 | 0.158 |
| 13 | 0.490 | −0.208 | 0.000 | −0.237 | 0.000 | −0.561 | 0.641 | 0.107 | 0.052 | 0.201 | 0.000 | 0.000 |
| 14 | 0.493 | 0.003 | 0.000 | −0.021 | 0.000 | 0.483 | 0.680 | 0.085 | 0.034 | 0.098 | 0.104 | 0.000 |
| 15 | 0.427 | −0.232 | 0.007 | −0.426 | 0.005 | −1.282 | 0.795 | 0.122 | 0.084 | 0.000 | 0.000 | 0.000 |
| 16 | 0.581 | 0.263 | −0.001 | 0.323 | −0.002 | −0.074 | 0.482 | 0.138 | 0.072 | 0.080 | 0.063 | 0.186 |

TABLE Y**-continued

| INTERVAL # | dV | $dT_{HIGH}$ | ddflow/dt | dmatch delta | dflow | $T_{INTERVAL}$-avg$T_{INTERVAL}$ | $T_{LOW}$ | $T_{HIGH}1$ | $T_{HIGH}2$ | $T_{HIGH}3$ | $T_{HIGH}4$ | $T_{HIGH}5$ |
|---|---|---|---|---|---|---|---|---|---|---|---|---|
| 17 | 0.611 | −0.249 | −0.027 | −0.085 | −0.003 | 0.175 | 0.311 | 0.128 | 0.128 | 0.057 | 0.066 | 0.253 |
| 18 | 0.537 | 0.072 | −0.038 | 0.026 | −0.005 | −0.194 | 0.589 | 0.213 | 0.100 | 0.058 | 0.038 | 0.190 |
| 19 | 0.565 | −0.037 | 0.009 | 0.011 | 0.001 | 0.509 | 0.511 | 0.114 | 0.076 | 0.029 | 0.038 | 0.170 |
| 20 | 0.611 | 0.153 | 0.000 | −0.049 | 0.000 | 0.313 | 0.400 | 0.133 | 0.101 | 0.051 | 0.125 | 0.250 |
| 21 | 0.576 | −0.059 | −0.001 | −0.104 | 0.001 | 0.315 | 0.427 | 0.117 | 0.073 | 0.040 | 0.350 | 0.000 |
| 22 | 0.530 | −0.178 | −0.025 | 0.006 | −0.002 | 0.211 | 0.541 | 0.142 | 0.030 | 0.050 | 0.215 | 0.000 |
| 23 | 0.566 | 0.108 | 0.000 | 0.027 | −0.001 | 0.117 | 0.462 | 0.145 | 0.038 | 0.060 | 0.162 | 0.131 |
| 24 | 0.466 | −0.546 | 0.000 | −0.214 | −0.001 | 0.283 | 0.712 | 0.128 | 0.073 | 0.059 | 0.000 | 0.000 |
| 25 | 0.539 | 0.273 | 0.000 | 0.021 | −0.001 | −0.462 | 0.492 | 0.073 | 0.051 | 0.174 | 0.090 | 0.000 |

**ALL VALUES ARE DIVIDED BY THE INTERVAL BETWEEN BASE AND MATCH POINTS ($T_{INTERVAL}$)

TABLE Z**

| INTERVAL # | dV | $dT_{HIGH}$ | ddflow/dt | dmatch delta | dflow | $T_{INTERVAL}$-avg$T_{INTERVAL}$ | x = −4 y = 0.3 | x = −4 y = 0.5 | x = −4 y = 0.7 | x = −4 y = 1 |
|---|---|---|---|---|---|---|---|---|---|---|
| 1 | 0.44 | 0.000 | −0.01 | 0.01 | −0.002 | −0.12 | 2.3 | 4.0 | 7.1 | 16.6 |
| 2 | 0.45 | 0.000 | 0.03 | −0.03 | 0.002 | −0.11 | 2.3 | 4.0 | 7.1 | 16.6 |
| 3 | 0.36 | 0.000 | 0.00 | −0.05 | 0.000 | 0.63 | 2.3 | 3.9 | 6.8 | 15.7 |
| 4 | 0.29 | 0.001 | −0.01 | −0.03 | 0.002 | −0.47 | 2.2 | 3.8 | 6.6 | 14.9 |
| 5 | 0.45 | 0.000 | 0.00 | 0.13 | 0.002 | −0.16 | 2.3 | 4.0 | 7.1 | 16.6 |
| 6 | 0.44 | 0.000 | 0.01 | 0.01 | −0.004 | 0.01 | 2.3 | 4.0 | 7.0 | 16.4 |
| 7 | 0.40 | 0.000 | −0.01 | −0.04 | 0.000 | −0.03 | 2.3 | 4.0 | 6.9 | 16.0 |
| 8 | 0.39 | 0.000 | 0.00 | −0.07 | 0.005 | 0.02 | 2.3 | 4.0 | 7.0 | 16.1 |
| 9 | 0.32 | 0.000 | −0.02 | −0.01 | −0.003 | −0.25 | 2.2 | 3.8 | 6.6 | 15.0 |
| 10 | 0.31 | 0.000 | 0.04 | 0.01 | 0.001 | −0.08 | 2.2 | 3.9 | 6.6 | 15.0 |
| 11 | 0.30 | 0.000 | −0.01 | −0.04 | 0.001 | −0.11 | 2.2 | 3.8 | 6.6 | 14.8 |
| 12 | 0.31 | 0.000 | −0.03 | 0.06 | −0.001 | 0.07 | 2.2 | 3.9 | 6.6 | 15.1 |
| 13 | 0.39 | 0.000 | 0.04 | 0.01 | −0.001 | −0.40 | 2.3 | 3.9 | 6.9 | 15.8 |
| 14 | 0.44 | 0.000 | 0.00 | 0.06 | 0.005 | −0.28 | 2.3 | 4.0 | 7.0 | 16.4 |
| 15 | 0.43 | 0.000 | 0.00 | −0.06 | 0.001 | 0.10 | 2.3 | 4.0 | 7.1 | 16.5 |
| 16 | 0.30 | 0.000 | 0.01 | −0.07 | −0.002 | −0.12 | 2.2 | 3.8 | 6.6 | 14.9 |
| 17 | 0.34 | 0.000 | 0.01 | 0.02 | −0.002 | −0.09 | 2.3 | 3.9 | 6.7 | 15.3 |
| 18 | 0.34 | 0.000 | 0.02 | −0.05 | 0.003 | 0.00 | 2.2 | 3.9 | 6.7 | 15.2 |
| 19 | 0.25 | 0.000 | 0.00 | −0.21 | 0.001 | −0.07 | 2.2 | 3.7 | 6.3 | 14.0 |
| 20 | 0.31 | 0.000 | 0.03 | −0.23 | 0.010 | −0.34 | 2.2 | 3.8 | 6.4 | 14.2 |
| 21 | 0.23 | 0.000 | −0.04 | 0.17 | −0.006 | 0.32 | 2.2 | 3.7 | 6.3 | 14.1 |
| 22 | 0.40 | 0.000 | −0.01 | 0.05 | 0.001 | 0.59 | 2.3 | 4.0 | 6.9 | 15.9 |
| 23 | 0.25 | 0.000 | −0.02 | 0.20 | 0.000 | 0.44 | 2.2 | 3.8 | 6.4 | 14.2 |
| 24 | 0.31 | 0.000 | −0.01 | −0.02 | 0.000 | 0.65 | 2.2 | 3.8 | 6.6 | 14.6 |
| 25 | 0.51 | 0.000 | 0.02 | 0.09 | 0.001 | −0.02 | 2.3 | 4.1 | 7.2 | 17.1 |

| INTERVAL # | x = −4 y = 1.5 | x = −4 y = 2 | x = −4 y = 2.4 | x = −2 y = 0.3 | x = −2 y = 0.5 | x = −2 y = 0.7 | x = −2 y = 1 | x = −2 y = 1.5 | x = −2 y = 2 |
|---|---|---|---|---|---|---|---|---|---|
| 1 | 69.7 | 299 | 973 | 2.2 | 3.8 | 6.5 | 14.6 | 58.0 | 237 |
| 2 | 70.1 | 302 | 987 | 2.2 | 3.8 | 6.5 | 14.6 | 58.3 | 239 |
| 3 | 63.5 | 262 | 824 | 2.2 | 3.7 | 6.2 | 13.7 | 52.1 | 203 |
| 4 | 58.2 | 229 | 890 | 2.1 | 3.6 | 6.0 | 12.9 | 47.1 | 174 |
| 5 | 69.8 | 300 | 978 | 2.2 | 3.8 | 6.5 | 14.6 | 58.1 | 237 |
| 6 | 68.3 | 291 | 944 | 2.2 | 3.7 | 6.4 | 14.4 | 56.7 | 230 |
| 7 | 65.5 | 273 | 886 | 2.2 | 3.7 | 6.3 | 14.0 | 54.0 | 213 |
| 8 | 65.8 | 272 | 855 | 2.2 | 3.7 | 6.3 | 14.1 | 54.2 | 212 |
| 9 | 58.6 | 231 | 698 | 2.1 | 3.6 | 6.0 | 13.0 | 47.4 | 175 |
| 10 | 59.2 | 236 | 720 | 2.1 | 3.6 | 6.0 | 13.0 | 48.1 | 180 |
| 11 | 57.6 | 226 | 680 | 2.1 | 3.6 | 5.9 | 12.8 | 46.6 | 171 |
| 12 | 59.4 | 237 | 720 | 2.1 | 3.6 | 6.0 | 13.1 | 48.2 | 180 |
| 13 | 64.2 | 265 | 831 | 2.2 | 3.7 | 6.2 | 13.8 | 52.8 | 206 |
| 14 | 68.2 | 288 | 923 | 2.2 | 3.8 | 6.4 | 14.4 | 56.5 | 226 |
| 15 | 69.2 | 294 | 951 | 2.2 | 3.8 | 6.5 | 14.5 | 57.5 | 232 |
| 16 | 58.4 | 231 | 696 | 2.1 | 3.6 | 6.0 | 12.9 | 47.3 | 175 |
| 17 | 50.8 | 245 | 752 | 2.2 | 3.6 | 6.1 | 13.3 | 49.5 | 187 |
| 18 | 60.1 | 241 | 737 | 2.2 | 3.6 | 6.0 | 13.2 | 48.9 | 184 |
| 19 | 52.7 | 199 | 578 | 2.1 | 3.5 | 5.7 | 12.0 | 41.9 | 147 |
| 20 | 54.2 | 207 | 605 | 2.1 | 3.5 | 5.8 | 12.3 | 43.3 | 154 |
| 21 | 53.8 | 210 | 631 | 2.1 | 3.4 | 5.7 | 12.1 | 43.1 | 157 |
| 22 | 65.6 | 276 | 885 | 2.2 | 3.7 | 6.3 | 13.9 | 54.1 | 216 |
| 23 | 54.0 | 208 | 615 | 2.1 | 3.5 | 5.7 | 12.2 | 43.2 | 155 |
| 24 | 58.4 | 235 | 726 | 2.1 | 3.5 | 5.9 | 12.8 | 47.4 | 180 |
| 25 | 73.5 | 323 | 1077 | 2.2 | 3.8 | 6.6 | 15.1 | 61.6 | 259 |

**ALL VALUES ARE DIVIDED BY THE INTERVAL BETWEEN BASE AND MATCH POINTS ($T_{INTERVAL}$)

What I claim is:

1. A method for estimating gas leakage from the ventilator circuit and patient interface that relies on breath-by-breath or time-to-time variability in the pattern of pressure delivery by the ventilator, which comprises:

generating signals that correspond to pressure ($P_{CIRCUIT}$) and flow rate (Flow) in the ventilator circuit, integrating Flow (Integrated Flow), measuring the change in Integrated Flow ($\Delta V$) over an INTERVAL extending from a selected point in the expiratory phase of a ventilator cycle to a selected point during the expiratory phase of a nearby ventilator cycle, repeating said measurement of $\Delta V$ in at least two said INTERVALs, processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALs and the corresponding differences in said index or indices of $P_{CIRCUIT}$, and establishing from said relation the leak rate at specified $P_{CIRCUIT}$ values.

2. The method of claim 1 wherein selected points in the expiratory phase are the end-expiratory points.

3. The method of claim 1 wherein the selected points delimiting INTERVAL are chosen so that Flow is similar at the two sampling points.

4. The method of claim 3 wherein selected points delimiting INTERVAL are chosen so that both Flow and the rate of change in Flow are similar at the two sampling points.

5. The method of claim 1 wherein each $\Delta V$ is divided by the duration of the INTERVAL over which it was measured to obtain an average Flow rate over the INTERVAL (Average Flow).

6. The method of claim 1 wherein processing of $P_{CIRCUIT}$ to produce an index or indices that reflect(s) the pattern of pressure delivery by the ventilator comprises determination of times spent in different pressure ranges (Times) within each INTERVAL, said Times serving as the Indices of pressure pattern.

7. The method of claim 6 wherein said Times are divided by the duration of the INTERVAL to obtain the fraction of time spent in said pressure ranges (Time Fractions).

8. The method of claim 1 wherein processing of $P_{CIRCUIT}$ to produce an index or indices that reflect(s) the pattern of pressure delivery by the ventilator comprises calculating the time courses of a plurality of specified mathematical functions of $P_{CIRCUIT}$ within each INTERVAL and integrating the resulting values of processed $P_{CIRCUIT}$ over the period of the INTERVAL, thereby resulting in a plurality of indices of pressure pattern (Integrals) within each INTERVAL, with each Integral corresponding to pressure processing using a specified mathematical function.

9. The method of claim 8 wherein Integrals are divided by the corresponding duration of the INTERVALs to obtain the average Integral (Average Integrals).

10. The method of claim 1 wherein processing of $P_{CIRCUIT}$ to produce an index or indices that reflect(s) the pattern of pressure delivery by the ventilator comprises calculating the times spent at a common reference high pressure and a common reference low pressure.

11. The method of claim 1 wherein statistical methods comprise regression analyses of the results obtained from a plurality of INTERVALs, with $\Delta V$ or Average Flow of each INTERVAL serving as the dependent variable and the index of indices of $P_{CIRCUIT}$ in the same INTERVALs serving as the independent variable(s).

12. The method of claim 11 wherein additional independent variables that reflect contribution of true changes in lung volume to $\Delta V$ are incorporated in the regression.

13. The method of claim 1 wherein the results of the statistical analysis performed on a plurality of previous INTERVALs are applied to current pressure values to estimate current gas leakage.

14. The method of claim 1 including a method for estimating variability in pattern of pressure delivery.

15. The method of claim 1 including a method for detecting a change in the leak characteristics.

16. A device for estimating gas leakage from the ventilator circuit and patient interface that relies on breath-by-breath or time-to-time variability in the pattern of pressure delivery by the ventilator, which comprises:

computer for storing and processing data corresponding to pressure ($P_{CIRCUIT}$) and flow rate (Flow) in the ventilator circuit, with said processing comprising:

algorithm(s) for integrating Flow (Integrated Flow), algorithm(s) for measuring the change in Integrated Flow ($\Delta V$) over an INTERVAL extending from a selected point in the expiratory phase of a ventilator cycle to a selected point during the expiratory phase of a nearby ventilator cycle, repeating said measurement of $\Delta V$ in at least two said INTERVALs, algorithm(s) for processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALs and the corresponding differences in said index or indices of $P_{CIRCUIT}$, establishing from said relation the leak rate at specified $P_{CIRCUIT}$ values.

17. The device of claim 16 wherein selected points in the expiratory phase are the end-expiratory points.

18. The device of claim 16 wherein the selected points delimiting INTERVAL are chosen so that Flow is similar at the two sampling points.

19. The device of claim 18 wherein selected points delimiting INTERVAL are chosen so that both Flow and the rate of change in Flow are similar at the two sampling points.

20. The device of claim 16 wherein each $\Delta V$ is divided by the duration of the INTERVAL over which it was measured to obtain an average Flow rate over the INTERVAL (Average Flow).

21. The device of claim 16 wherein processing of $P_{CIRCUIT}$ to produce an index or indices that reflect(s) the pattern of pressure delivery by the ventilator comprises determination of times spent in different pressure ranges (Times) within each INTERVAL, said Times serving as the Indices of pressure pattern.

22. The device of claim 21 wherein said Times are divided by the duration of the INTERVAL to obtain the fraction of time spent in said pressure ranges (Time Fractions).

23. The device of claim 16 wherein processing of $P_{CIRCUIT}$ to produce an index or indices that reflect(s) the pattern of pressure delivery by the ventilator comprises calculating the time courses of a plurality of specified mathematical functions of $P_{CIRCUIT}$ within each INTERVAL and integrating the resulting values of processed $P_{CIRCUIT}$ over the period of the INTERVAL, thereby resulting in a plurality of indices of pressure pattern (Integrals) within each INTERVAL, with each Integral corresponding to pressure processing using a specified mathematical function.

24. The device of claim 23 wherein Integrals are divided by the corresponding duration of the INTERVALs to obtain the average Integral (Average Integrals).

25. The device of claim 16 wherein processing of $P_{CIRCUIT}$ to produce an index or indices that reflect(s) the pattern of pressure delivery by the ventilator comprises calculating the times spent at a common reference high pressure and a common reference low pressure.

26. The device of claim 16 wherein statistical methods comprise regression analyses of the results obtained from a plurality of INTERVALs, with $\Delta V$ or Average Flow of each INTERVAL serving as the dependent variable and the index of indices of $P_{CIRCUIT}$ in the same INTERVALs serving as the independent variable(s).

27. The device of claim 26 wherein additional independent variables that reflect contribution of true changes in lung volume to $\Delta V$ are incorporated in the regression.

28. The device of claim 16 wherein the results of the statistical analysis performed on a plurality of previous INTERVALs are applied to current pressure values to estimate current gas leakage.

29. The device of claim 16 including algorithms for estimating variability in pattern of pressure delivery.

30. The device of claim 16 including algorithms for detecting a change in the leak characteristics.

31. A computer readable medium having a computer program stored thereon for estimating gas leakage from the ventilator circuit and patient interface that relies on breath-by-breath or time-to-time variability in the pattern of pressure delivery by the ventilator, the computer program comprising:
   program code for receiving signals that correspond to pressure ($P_{CIRCUIT}$) and flow rate (Flow) in the ventilator circuit,
   program code for integrating Flow (Integrated Flow),
   program code for measuring the change in Integrated Flow ($\Delta V$) over an INTERVAL extending from a selected point in the expiratory phase of a ventilator cycle to a selected point during the expiratory phase of a nearby ventilator cycle,
   program code for repeating said measurement of $\Delta V$ in at least two said INTERVALs,
   program code for, based on $P_{CIRCUIT}$, producing an index or indices that reflect(s) the pattern of pressure delivery by the ventilator during each of said INTERVALs,
   program code for applying statistical methods to determine the relation between the differences in $\Delta V$ among INTERVALs and the corresponding differences in said index or indices of $P_{CIRCUIT}$,
   program code for establishing from said relation the leak rate at specified $P_{CIRCUIT}$ values.

32. A system for estimating gas leakage from the ventilator circuit and patient interface that relies on breath-by-breath or time-to-time variability in the pattern of pressure delivery by the ventilator, the system comprising:
   a processing structure and a computer readable medium accessible by the processing structure for storing and processing data corresponding to pressure ($P_{CIRCUIT}$) and flow rate (Flow) in the ventilator circuit, wherein the processing is performed by integrating Flow (Integrated Flow), measuring the change in Integrated Flow ($\Delta V$) over an INTERVAL extending from a selected point in the expiratory phase of a ventilator cycle to a selected point during the expiratory phase of a nearby ventilator cycle, repeating said measurement of $\Delta V$ in at least two said INTERVALs, processing $P_{CIRCUIT}$ to produce an index or indices that reflect(s) the pattern of pressure delivery by the ventilator during each of said INTERVALs, applying statistical methods to determine the relation between the differences in $\Delta V$ among INTERVALS and the corresponding differences in said index or indices of $P_{CIRCUIT}$, and establishing from said relation the leak rate at specified $P_{CIRCUIT}$ values.

* * * * *